US008637675B2

(12) United States Patent
Priebe et al.

(10) Patent No.: US 8,637,675 B2
(45) Date of Patent: *Jan. 28, 2014

(54) INHIBITORS OF PROLIFERATION AND ACTIVATION OF SIGNAL TRANSDUCER AND ACTIVATORS OF TRANSCRIPTION (STATS)

(75) Inventors: Waldemar Priebe, Houston, TX (US); Stanislaw Skora, Houston, TX (US); Timothy Madden, Sugarland, TX (US); Izabela Fokt, Houston, TX (US); Charles Conrad, Spring, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/401,161

(22) Filed: Feb. 21, 2012

(65) Prior Publication Data

US 2012/0149738 A1  Jun. 14, 2012

Related U.S. Application Data

(63) Continuation of application No. 12/989,944, filed as application No. PCT/US2009/048782 on Jun. 26, 2009, now Pat. No. 8,143,412.

(60) Provisional application No. 61/079,002, filed on Jul. 8, 2008.

(51) Int. Cl.
    *A61K 31/44*     (2006.01)
    *C07D 213/57*    (2006.01)

(52) U.S. Cl.
    USPC .......................................... 546/330; 514/345

(58) Field of Classification Search
    None
    See application file for complete search history.

(56) References Cited

U.S. PATENT DOCUMENTS

| | | | |
|---|---|---|---|
| 4,414,150 A | 11/1983 | Goeddel | |
| 4,456,748 A | 6/1984 | Goeddel | |
| 4,678,751 A | 7/1987 | Goeddel | |
| 4,695,629 A | 9/1987 | Clauss et al. | |
| 4,766,106 A | 8/1988 | Katre et al. | |
| 4,897,471 A | 1/1990 | Stabinsky | |
| 4,917,888 A | 4/1990 | Katre et al. | |
| 4,999,357 A | 3/1991 | Gadras et al. | |
| 5,196,446 A | 3/1993 | Levitzki et al. | |
| 5,541,293 A | 7/1996 | Priebe et al. | |
| 5,643,575 A | 7/1997 | Martinez et al. | |
| 5,700,822 A | 12/1997 | Hirth et al. | |
| 5,711,944 A | 1/1998 | Gilbert et al. | |
| 5,738,846 A | 4/1998 | Greenwald et al. | |
| 5,773,476 A | 6/1998 | Chen et al. | |
| 5,854,285 A | 12/1998 | Sriram et al. | |
| 5,919,455 A | 7/1999 | Greenwald et al. | |
| 5,951,974 A | 9/1999 | Gilbert et al. | |
| 5,981,569 A | 11/1999 | App et al. | |
| 6,042,822 A | 3/2000 | Gilbert et al. | |
| 6,113,906 A | 9/2000 | Greenwald et al. | |
| 6,194,453 B1 | 2/2001 | Sriram et al. | |
| 6,225,346 B1 | 5/2001 | Tang et al. | |
| 6,313,153 B1 | 11/2001 | Hasegawa et al. | |
| 6,331,555 B1 | 12/2001 | Hirth et al. | |
| 6,420,338 B1 | 7/2002 | Schneider et al. | |
| 6,426,366 B1 | 7/2002 | Novogrodsky et al. | |
| 6,433,018 B1 | 8/2002 | Siddiqui et al. | |
| 6,555,702 B2 | 4/2003 | Sriram et al. | |
| 6,596,828 B1 | 7/2003 | Kaita et al. | |
| 6,596,878 B2 | 7/2003 | Chen et al. | |
| 6,610,830 B1 | 8/2003 | Goeddel et al. | |
| 7,235,588 B2 | 6/2007 | Siddiqui et al. | |
| 7,745,468 B2 | 6/2010 | Priebe et al. | |
| 7,807,719 B2 * | 10/2010 | Roifman et al. | 514/557 |
| 2002/0045191 A1 | 4/2002 | Schneider et al. | |
| 2002/0115714 A1 | 8/2002 | Sriram et al. | |
| 2003/0013748 A1 | 1/2003 | Novogrodsky et al. | |
| 2003/0032596 A1 | 2/2003 | Schneider et al. | |
| 2004/0030101 A1 | 2/2004 | Bailon et al. | |
| 2005/0277680 A1 | 12/2005 | Priebe et al. | |
| 2006/0030536 A1 | 2/2006 | Yu et al. | |
| 2006/0058297 A1 | 3/2006 | Roifman et al. | |
| 2006/0147436 A1 | 7/2006 | Revel et al. | |
| 2007/0232668 A1 | 10/2007 | Priebe et al. | |
| 2008/0167277 A1 | 7/2008 | Conrad et al. | |
| 2009/0163545 A1 | 6/2009 | Goldfarb | |
| 2010/0152143 A1 | 6/2010 | Priebe et al. | |

FOREIGN PATENT DOCUMENTS

| | | |
|---|---|---|
| CA | 2092017 | 9/1993 |
| DE | 1 212 984 | 3/1966 |
| DE | 2 555 789 | 7/1977 |
| DE | 4 330 105 | 3/1993 |
| EP | 0 537 742 | 4/1993 |
| EP | 1 000 935 | 5/2000 |
| JP | 41-3540 | 3/1966 |
| JP | 05-301838 | 11/1993 |

(Continued)

OTHER PUBLICATIONS

EPO Communication Extended Supplementary Search Report and Search Opinion EP 09 794 969.7, Mar. 16, 2012.
"Design, Synthesis and Structure-Activity Relationships of Novel Jak2/STAT3 Signaling Inhibitors," AACR Abtract Later Breaking News, Feb. 1, 2006 (Abstract No. 06-LBA-8902-AACR).
Alas and Bonavida, "Inhibition of constitutive STAT3 activity sensitizes resistant non-Hodgkin's lymphoma and multiple myeloma to chemotherapeutic drug-mediated apoptosis," *Clin. Cancer Res.*, 9(1):316-26, 2003.
Alcon et al., "Activation of Tyrosine Kinase Pathway by Vanadate in Gallbladder Smooth Muscle," *Biochem. Pharmacol.*, 59:1077-1089, 2000.

(Continued)

*Primary Examiner* — Janet Andres
*Assistant Examiner* — Heidi Reese
(74) *Attorney, Agent, or Firm* — Parker Highlander PLLC

(57) ABSTRACT

Pyridine compounds effective in modulation STAT3 and/or STAT5 activation are provided that are useful in the prevention and treatment of proliferative disease and conditions including cancer, inflammation and proliferative skin disorders.

16 Claims, 3 Drawing Sheets

(56) References Cited

FOREIGN PATENT DOCUMENTS

| | | |
|---|---|---|
| JP | 06-247850 | 9/1994 |
| JP | 07-188145 | 7/1995 |
| JP | 2000-204070 | 7/2000 |
| JP | 2003-119169 | 4/2003 |
| WO | WO 91-16305 | 10/1991 |
| WO | WO 95-14464 | 6/1995 |
| WO | WO 95-18606 | 7/1995 |
| WO | WO 95-19169 | 7/1995 |
| WO | WO 95-24190 | 9/1995 |
| WO | WO 95-26341 | 10/1995 |
| WO | WO 95-28922 | 11/1995 |
| WO | WO 98-06391 | 2/1998 |
| WO | WO 98-036101 | 8/1998 |
| WO | WO 99/05109 | 2/1999 |
| WO | WO 02-078617 | 10/2002 |
| WO | WO 03-068157 | 8/2003 |
| WO | WO 03-073999 | 9/2003 |
| WO | WO 03-086396 | 10/2003 |
| WO | WO 2004-047743 | 6/2004 |
| WO | WO 2005-000777 | 1/2005 |
| WO | WO 2005-053671 | 6/2005 |
| WO | WO 2005-058829 | 6/2005 |
| WO | WO 2005-092904 | 10/2005 |
| WO | WO 2006-029515 | 3/2006 |
| WO | WO 2006-057824 | 6/2006 |
| WO | WO 2006-086422 | 8/2006 |
| WO | WO 2007-006143 | 1/2007 |
| WO | WO 2007-092278 | 8/2007 |
| WO | WO 2007-115269 | 10/2007 |
| WO | WO 2007-130523 | 11/2007 |
| WO | WO 2008-005954 | 1/2008 |
| WO | WO 2008-079460 | 7/2008 |
| WO | WO 2008-083389 | 7/2008 |
| WO | WO 2008-118445 | 10/2008 |
| WO | WO 2008-121858 | 10/2008 |
| WO | WO 2009-036101 | 3/2009 |
| WO | WO 2009-073575 | 6/2009 |
| WO | WO 2009-091506 | 7/2009 |
| WO | WO 2010-005807 | 1/2010 |
| WO | WO 2010-081158 | 7/2010 |

OTHER PUBLICATIONS

Arbelet al., "Inhibitors that target protein kinases for the treatment of ovarian carcinoma," *Am. J Obstet. Gynecol.*, 188(5):1283-90, 2003.
Bartholomeuszet al., "Degrasyn activates proteasomal-dependent degradation of c-Myc," *Cancer Research*, 67(8):3912-3918, 2007.
Bartonet al., "Signal transducer and activator of transcription 3 (STAT3) activation in prostate cancer: direct STAT3 inhibition induces apoptosis in prostate cancer lines," Molecular Cancer Therapeutics, 3(1):11-20, 2004.
Bhartiet al., "Curcumin (diferuloylmethane) inhibits constitutive and IL-6-inducible STAT3 phosphorylation in human multiple myeloma cells," *J. Immunol.*, 171(7):3863-3871, 2003.
Burdelyaet al., "Combination therapy with AG-490 and interleukin 12 achieves greater antitumor effects than either agent alone," *Mol. Cancer Ther.*, 1(11):893-9, 2002.
Burkeet al., "Inhibition of constitutively active Stat3 suppresses growth of human ovarian and breast cancer cells," *Oncogene*, 20:7925-7934, 2001.
CAS RN 324567-34-2, STN Entry Date Feb. 27, 2001.
CAS RN 340313-80-6, STN Entry Date Jul. 11, 2001.
CAS RN 345368-05-0, STN Entry Date Jul. 11, 2001.
CAS RN 345368-07-2, STN Entry Date Jul. 11, 2001.
CAS RN 345368-66-3, STN Entry Date Jul. 11, 2001.
CAS RN 358284-16-9, STN Entry Date Sep. 23, 2001.
CAS RN 358284-17-0, STN Entry Date Sep. 23, 2001.
CAS RN 358314-79-1, STN Entry Date Sep. 23, 2001.
CAS RN 364796-80-5, STN Entry Date Oct. 26, 2001.
CAS RN 444320-16-5, STN Entry Date Aug. 20, 2002.
CAS RN 444552-66-3, STN Entry Date Aug. 21, 2002.
CAS RN 444685-73-8, STN Entry Date Aug. 22, 2002.
CAS RN 455327-12-5, STN Entry Date Sep. 26, 2002.
CAS RN 474913-20-7, STN Entry Date Dec. 3, 2002.
CAS RN 477972-63-7, STN Entry Date Jan. 2, 2003.
CAS RN 478017-59-3, STN Entry Date Jan. 3, 2003.
CAS RN 478017-92-4, STN Entry Date Jan. 3, 2003.
CAS RN 502884-84-6, STN Entry Date Apr. 14, 2003.
CASRN 477972-73-9, STN Entry Date Jan. 2, 2003.
Catlett-Falconeet al., "Constitutive activation of Stat3 signaling confers resistance to apoptosis in human U266 myeloma cells," *Immunity*, 10(1): 105-15, 1999.
Chenet al., "Crystal structure of a tyrosine phosphorylated STAT-1 dimer bound to DNA," *Cell*, 93:827-839, 1998.
Chenet al., "Human pancreatic adenocarcinoma: in vitro and in vivo morphology of a new tumor line established from ascites," *In Vitro*, 18(1):24-34, 1982.
Constantinet al., "Tyrphostin AG490, a tyrosine kinase inhibitor, blocks actively induced experimental autoimmune encephalomyelitis," *Eur. J Immunol.*, 28(11):3523-9, 1998.
Darnell, "Validating stat3 in cancer therapy," *Nature Medicine*, 11(6):595-596, 2005.
Database Crossfire Beilstein, Accession No. 9145100, 2002.
De Voset al., "JAK2 tyrosine kinase inhibitor tyrphostin AG490 downregulates the mitogen-activated protein kinase (MAPK) and signal trasducer and activator of transcription (STAT) pathways and induces apoptosis in myeloma cells," *Br. J. Haematol.* 109:823-828, 2000.
Duqueet al., "Structure of N-benzyl-[Duqueet al., Structure of N-benzyl-[2-cyano-3-(2'-furyl)acrylamide], Revista CENIC," *Ciencias Quimicas*, 27(1-2-3):25-29, 1996.
Durruthyet al., "Structure of N-(2-furylmethyl)-alpha-cyano-2-furanacrylamide," *Acta Crystallographica, Section C: Crystal Structure Communications*, C49(3):558-559, 1993.
Epling-Burnetteet al., "Inhibition of STAT3 signaling leads to apoptosis of leukemic large granular lymphocytes and decreased Mcl-1 expression," The Journal of Clinical Investigation, 107(3):351-362, 2001.
Examiner's search strategy and results for U.S. Appl. No. 12/824,901, dated Oct. 17, 2011.
Farooki et al,. "Tyrphostins disrupt stress fibers and cellular attachments in endothelial monolayers," *Exp. Cell Res.*, 243(1):185-198, 1998.
Ferrajoliet al., "WP1066 disrupts janus kinase-2 and induces caspase-dependent apoptosis in acute myelogenous leukemia cells," *Cancer Research*, 67(23):11291-11299, 2007.
Garciaet al., "Constitutive activation of Stat3 by the Src and JAK tyrosine kinases participates in growth regulation of human breast carcinoma cells," Oncogene, 20:2499-2513, 2001.
Gazitet al., "Tyrphostins. 2. Heterocyclic and alpha-substituted benzylidenomalononitrile tyrphostins as potent inhibitors of EG receptor and ErbB2/nue tyrosine kinases," *J Med. Chem.*, 34(6):1896-1907, 1991.
Gazit,et al., "Tyrphostins I: synthesis and biological activity of protein tyrosine kinase inhibitors," *J Med. Chem.*, 32:2344-2352, 1989.
Halleket al., "Multiple myeloma: increasing evidence for a multistep transformation process," *Blood*, 91(1):3-21, 1998.
Hcaplus 2005:246273.
Heinrichet al., "Interleukin-6-type cytokine signaling through the GP130/Jak/STAT pathway 1," *Biochem J.*, 334:297-314, 1998.
Hernandezet al., "2-cyano-N-furfuryl-3-(2-furyl)acrylamide," *Acta Crystallographica, Section C: Crystal Structure Communications*, C52(1):203-205, 1996.
Hideshimaet al., "NF-kappa B as a therapeutic target in multiple myeloma," *J. Biol. Chem.*, 277(19):16639-16647, 2002.
Horiguchiet al., "STAT3 inhibitor WP1066 as a novel therapeutic agent for renal cell carcinoma," British Journal of Cancer, 102(11):1592-1599, 2010.
Huang, "Regulation of metastases by signal transducer and activator of transcription 3 signaling pathway: clinical implications," *Clin Cancer Res*, 13(5):1362-1366, 2007.
Hussainet al., "A novel small molecule inhibitor of signal transducers and activators of transcription 3 reverses immune tolerance in malignant glioma patients," *Cancer Research*, 67(20):9630-9636, 2007.

(56) References Cited

OTHER PUBLICATIONS

Iwamaru et al., "A novel inhibitor of the STAT3 pathway induces apoptosis in malignant glioma cells both in vitro and in vivo," *Oncogene*, 26(17):2435-2444, 2007.
Jernberg-Wiklund et al., "Expression of myc-family genes in established human multiple myeloma cell lines: L-myc but not c-myc gene expression in the U-266 myeloma cell line," *Int. J. Cancer*, 51(1):116-123, 1992.
Kamath and Buolamwini, "Receptor-guided alignment-based comparative 3D-QSAR studies of benzylidene malonitrile tyrphostins as EGFR and HER-2 kinase inhibitors," J. Med. Chem., 46:4657-4668, 2003.
Kerr et al., "Of JAKs, STATs, blind watchmakers, jeeps and trains," *FEBS Lett.*, 546(1):1-5, 2003.
Kijima et al., "STAT3 activation abrogates growth factor dependence and contributes to head and neck squamous cell carcinoma tumor growth in vivo," *Cell Growth Differ*, 13:355-362, 2002.
Kirken et al., "Tyrphostin AG0490 inhibits cytokine-mediated JAK3/STAT5a/b signal transduction and cellular proliferation of antigen-activated human T cells," *J.Leukoc. Biol.*, 65:891-899, 1999.
Kisseleva et al., "Signaling through the JAK/STAT pathway, recent advances and future challenges," *Gene*, 285:1-24, 2002.
Kong et al., "A novel inhibitor of signal transducers and activators of transcription 3 activation is efficacious against established central nervous system melanoma and inhibits regulatory T cells," *Clinical Cancer Research*, 14(18):5759-5768, 2008.
Kong et al., "A novel phosphorylated STAT3 inhibitor enhances T cell cytotoxicity against melanoma through inhibition of regulatory T cells," *Cancer Immunology Immunotherapy*, 58(7):1023-1032, 2009.
Kuehl et al., "Dysregulation of c-myc in multiple myeloma," *Curr. Top Microbiol. Immunol.*, 224:277-282, 1997.
Kupferman et al., "Therapeutic suppression of constitutive and inducible JAK/STAT activation in head and neck squamous cell carcinoma," *Journal of Experimental Therapeutics and Oncology*, 8(2):117-127, 2009.
Lee et al., "Flavopiridol disrupts STAT3/DNA interactions, attenuates STAT3-directed transcription, and combines with the Jak kinase inhibitor AG490 to achieve cytotoxic synergy," Mol Cancer Ther, 5(1):138-148, 2006.
Levitzki, "Tyrphostins: tyrosine kinase blockers as novel antiproliferative agents and dissectors of signal transduction," *FASEB Journal*, 6:3275-82, 1992.
Levy et al., "STAT3: a multifaceted oncogene," *PNAS*, 103(27):10151-10152, 2006.
Levy et al., "What does stat3 do?," *The Journal of Clinical Investigation*, 109(9), 2002.
Lieber et al., "Establishment of a continuous tumor-cell line (panc-1) from a human carcinoma of the exocrine pancreas," *Int. J Cancer*, 15(5):741-747, 1975.
Liu and Kern, "Neuregulin-1 activates the JAK-STAT pathway and regulates lung epithelial cell proliferation," Am. J. Respir. Cell Mol. Biol., 27:306-313, 2002.
Liu et al., "Immunohistochemical localization of activated stat3 and hTERT protein in psoriasis vulgaris," *Eur J Dermatol.*, 16(2):205-206, 2006.
Meydan et al, "Inhibition of acute lymphoblastic leukaemia by a Jak-2 inhibitor," *Nature* 379:645-648, 1996.
Morgan et al., "Human cell line (colo 357) of metastatic pancreatic adenocarcinoma," *Int. J Cancer*, 25(5):591-598, 1980.
Murata et al., "Synthesis and structure-activity relationships of novel IKK-b inhibitors, Part 3: orally active anti-inflammatory agents," *Bioorganic & Medicinal Chemistry Letters*, 14:4019-4022, 2004.
Nielsen et al., "Constitutive activation of a slowly migrating isoform of Stat3 in mycosis fungoides: Tyrphostin AG490 inhibits Stat3 activation and growth of mycosis fungoides tumor cell lines," Proc. Natl. Acad. Sci. USA, 94:6764-6769, 1997.
Nikitakis et al., "Targeting the STAT pathway in head and neck cancer: recent advances and future prospects," *Current Cancer Drug Targets*, 4:637-651, 2004.
Niu et al., "Roles of activated Src and Stat3 signaling in melanoma tumor cell growth," Oncogene, 21(46):7001-7010, 2002.
Office Action issued in Australian Application No. 2004298511, mailed Jun. 21, 2010.
Office Action issued in Australian Application No. 2007234455, mailed Sep. 6, 2011.
Office Action issued in Australian Patent Application No. 2011239276, dated May 4, 2012.
Office Action issued in Canadian Application No. 2,548,152, dated May 19, 2011.
Office Action issued in Canadian Application No. 2,548,152, mailed Feb. 7, 2012.
Office Action issued in Chinese Application No. 200480037045, English language translation, dated Jan. 28, 2011.
Office Action issued in Chinese Application No. 200480037045 (English language translation), mailed Jul. 24, 2009.
Office Action issued in Chinese Application No. 200780019917.4 (and English language translation), dated Aug. 24, 2011.
Office Action issued in European Application No. 04 813 958.8, mailed Jan. 11, 2011.
Office Action issued in European Application No. 07 759 977.7, mailed Apr. 16, 2010.
Office Action issued in Indian Application No. 3155/DELNP/2006, dated Jan. 31, 2011.
Office Action issued in Japanese Application No. 2006-544085, mailed Sep. 21, 2010.
Office Action issued in Korean Application No. 10-2006-7013861, mailed Jun. 22, 2011.
Office Action issued in Korean Application No. 10-2011-7027869, mailed Feb. 21, 2012.
Office Action issued in Mexican Application No. PA/a/2006/006460 (memo translating the requirements stated by the examiner), dated Nov. 4, 2009.
Office Action issued in Mexican Application No. PA/a/2006/006460 (memo translating the requirements stated by the examiner), dated Jul. 23, 2009.
Office Action issued in Russian Application No. 2008143237, mailed Mar. 28, 2011.
Office Action issued in U.S. Appl. No. 11/010,834, mailed Feb. 11, 2009.
Office Action issued in U.S. Appl. No. 11/010,834, mailed Jul. 24, 2008.
Office Action issued in U.S. Appl. No. 11/010,834, mailed Nov. 12, 2009.
Office Action issued in U.S. Appl. No. 11/695,547, mailed Feb. 26, 2009.
Office Action issued in U.S. Appl. No. 11/695,547, mailed May 25, 2010.
Office Action issued in U.S. Appl. No. 11/695,547, mailed Sep. 10, 2009.
Office Action issued in U.S. Appl. No. 12/307,088 mailed Aug. 2, 2011.
Office Action issued in U.S. Appl. No. 12/824,901, mailed Jun. 3, 2011.
Office Action issued in U.S. Appl. No. 13/350,637, mailed Dec. 13, 2012.
Pardanani, "JAK2 inhibitor therapy in myeloproliferative disorders: rationale, preclinical studies and ongoing clinical trials," *Leukemia*, 22:23-30, 2008.
PCT International Preliminary Report on Patentability issued in International Application No. PCT/US2004/041712, dated Jun. 12, 2006.
PCT International Search Report and Written Opinion issued in International Application No. PCT/US2007/065805, mailed Oct. 17, 2007.
PCT International Search Report issued in International Application No. PCT/US2004/041712, mailed Apr. 14, 2005.
PCT International Search Report issued in International Application No. PCT/US2007/072693, mailed Dec. 17, 2007.
Pomes et al., "Structure of N-(2-furfuryl)-2-cyano-3-(5-nitro-2-furyl)acrylamide," *Anales de la Asociacion Quimica Argentina*, 82(4):249-255, 1994.

(56) References Cited

OTHER PUBLICATIONS

Rahamanet al., "Inhibition of constitutively active Stat3 suppresses proliferation and induces apoptosis in glioblastoma multiforme cells," *Oncogene*, 21:8404-8413, 2002.
Renglinet al., "Miotic aberrations induced by carbaryl reflect tyrosine kinase inhibition with coincident up-regulation of serine/threonine protein phosphatase activity: implications for coordination of karyokinesis and cytokinesis," *Mutagenesis*. 14(3):327-334, 1999.
Saikachiet al., "Synthesis of furan derivatives. XVIII. 2-cyano-3(5-nitro-2-furyl)acrylamides and esters," *Chem. & Pharm. Bull.* (Tokyo), 7:453-456, 1959.
Satyamoorthyet al., "Melanoma cell lines from different stages of progression and their biological and molecular analyses," *Melanoma Res.*, 7(Suppl.2):S35-S42, 1997.
Schepetkinet al., "Novel small-molecule inhibitors of anthrax lethal factor indentified by high-throughput screening," *Journal of Medicinal Chemistry*, 49(17):5232-5244, 2006.
Seidelet al., "Pharmaceutical intervention in the JAK/STAT signaling pathway," *Oncogene*, 19:2645-2656, 2000.
Selvanayagamet al., "Alternation and Abnormal Expression of the c-myc Oncogene in Human Multiple Myeloma," *Blood*, 71(1):30-35, 1988.
Silverman, "The organic chemistry of drug design and drug addiction," Second Edition, *Elsevier*, pp. 29-32, 2004.
Songet al., "Activation of Stat3 by receptor tyrosine kinases and cytokines regulates survival in human non-small cell carcinoma cells," *Oncogene*, 22:4150-4165, 2003.
Songet al., "STAT signaling in head and neck cancer," *Oncogene*, 19:2489-2495, 2000.
Sunet al., "Cucurbitacin Q: a selective STAT3 activation inhibitors with potent antitumor activity," *Oncogene*, 24:3236-3245, 2005.
Supplementary European Search Report issued in European Application No. 04 813 958.8, mailed Oct. 10, 2008.
Tamizet al., "Structure-activity relationship of n-(phenylalkyl) cinnamides as novel NR2B subtype-selective NMDA receptor antagonists," *J. of Medicinal Chemistry*, 42:3412-20, 1999.
Tefferiet al., "JAK2 in myeloproliferative disorders is not just another kinase," *Cell Cycle*, 4(8):1053-1056, 2005.
Trajkovski, "STAT3-A promising molecular target for cancer therapy," *University of Toronto Medical Journal*, 83:16, 2005.
Vermaet al., "Jak family of kinases in cancer," *Cancer Metastasis Rev.*, 22(4):423-434, 2003.
Verstovseket al., "WP1066, a novel JAK2 inhibitor, suppresses proliferation and induces apoptosis in erythroid human cells carrying the JAK2 V617F mutation," *Clinical Cancer Research*, 14(3):788-796, 2008.
Vezeridiset al., "Heterogeneity of potential for hematogenous metastasis in a human pancreatic carcinoma," *J. Surg. Res.*, 48(1):51-55, 1990.
Vezeridiset al., "In vivo selection of a highly metastatic cell line from a human pancreatic carcinoma in the nude mouse," *Cancer*, 69(8):2060-2063, 1992.
Volberg et al, "Disruption of Microtubules in Living Cells by Tyrphostin AG-1714," *Cell Motility and the Cytoskelton*, 45(3):223-234; 2000.
Wanget al., "JAK3, STAT, and MAPK signaling pathways as novel molecular target for the tyrphostin AG-490 regulation of IL-2-mediated T cell response," *J. Immunol*, 162:3897-3904, 1999.
Xieet al., "Activation of Stat3 in human melanoma promotes brain metastasis," *Cancer Res.*, 66(6)3186-3196, 66(6)3186-3196, 2006.
Xieet al., "Stat3 activation regulates the expression of matrix metalloproteinase-2 and tumor invasion and metastasis," *Oncogene*, 23:3550-3560, 2004.
Yu and Jove, "The stats of cancer-new molecular targets come of age," *Nature Rev. Cancer*, 4(2):97-105, 2004.
Zlotniket al., "Tyrphostins reduce chemotherapy-induced intestinal injury in mice: assessment by a biochemical assay," *Br. J. Cancer*, 92(2):294-297, 2005.

Abdel-Latif et al., "Heterocycles synthesis through reactions of nucleophiles with acrylonitriles: Part III," *Indian Journal of Chemistry*, 29B:322-5, 1990.
Blum et al., "Substrate Competitive Inhibitors of IGF-1 Receptor Kinase," *Biochemistry*, 39:15705-15712, 2000.
Cocco et al., "Reaction of enaminonitriles with isocyanates. Synthesis of new 2-oxo and 6-oxopyrimadines," *Journal of Heterocyclic Chemistry*, 31:329-34, Hcaplus Abstract 457456, 1994.
Database CA, Accession No. 478235, 1990.
Database CA, Accession No. 584231, 1977.
Database CA, Accession No. 96215, 1999.
Duque et al., Structure of n-benzyl-(2-cyano-3-(2' furyl)-acrylamide), Crystal Structure Communications, 52(1):25-29, 1996.
Gadina et al., "Signaling by type I and type II cytokine receptors: ten years after," *Curr. Opin. Immunol.*, 13:363, 2001.
Hasegawa et al., "Preparation of pyridylacrylamide derivatives as TGF-beta inhibitors and therapeutic agents for nephritis," STN Database accession No. 1999:96215, Feb. 4, 1999.
Hebenstreit et al., "JAK/STAT-dependent gene regulation by cytokines," *Drug News Perspect.*, 18(4):243-249, 2005.
Hellgren et al., "The growth hormone receptor associates with Jak1, Jak2 and Tyk2 in human liver," *Growth Horm IGF Res*, 9(3):212-218, 1999.
Holmes, "Structure-activity relationships for some conjugates heteroenoid compounds catechol monoethers and morphine alkaloids," Defense Research Establishment Suffield, Ralston, Alberta, Canada, pp. 649-660, 1975.
Horvath, "The Jak-STAT pathway stimulated by interferon gamma," *Science*, STKE, 260:tr8, 2004.
Kampe et al., "Cyanoacetic acid anilide derivatives," STN Database accession No. 1977:584231, Jul. 7, 1977.
Levitzki et al., "Tyrphostins-Potential antiproliferative agents and novel molecular tools," *Biochem. Pharmacol*. 40:913-918, 1990.
Levitzki, "Protein Kinase Inhibitors as a Therapeutic Modality," *Acc. Chem. Res.*, 36:462-469, 2003.
Marko et al., "Cyclic 3'5'- nucleotide phosphodiesterases: potential targets for anticancer therapy," *Chem. Res. Toxicol.*, 13:944-948, 2000.
O'Shea et al., "A new modality for immunosuppression: targeting the JAK/STAT pathway," *Nature Rev. Drug Disc.*, 3:555-564, 2004.
Office Action issued in Chinese Application No. 200980135799.2, mailed May 6, 2013.
Office Action issued in Chinese Application No. 200780019917.4, mailed Apr. 25, 2013.
Office Action issued in U.S. Appl. No. 13/350,637, mailed Jun. 19, 2013.
Agarwala et al., "Interferons in melanoma," *Curr Opin Oncol*, 8:167-174, 1996.
Aliosi, "Immune function of microglia," *Glia*, 36:165-179, 2001.
Alterman et al., "B16 melanoma spontaneous brain metastasis: occurrence and development within leptomeninges blood vessels," *Clin Exp Metastasis*, 7:15-23, 1989.
Attia et al., "Inability of a fusion protein of IL-2 and diphtheria toxin (denileukin diftitox, DAB389I1-2, ONTAK) to eliminate regulatory T lymphocytes in patients with melanoma," *J Immunother*, 28:582-592, 2005.
Ausubel et al., "Current protocols in molecular biology," NY, John Wiley & Sons (and periodic supplements), Chapters 9, 13 and 16, 1995.
Bao et al , "Inhibition of constitutively active STAT3 by WP1066 suppresses proliferation and induces apoptosis in pancreatic cancer cells," *Clin Cancer Res*, 11:9026S-9027S, 2005.
Berd et al., "Effect of low dose cyclophosphamide on the immune system of cancer pateints: reduction of T-suppressor function without depletion of the CD8+ subset," *Cancer Res*, 47:3317-3321, 1987.
Bettelli et al., "$T_h$-17 cells in the circle of immunity and autoimmunity," *Nat Immunol*, 8:345-350, 2007.
Blaskovich et al., "Discovery of JSI-124 (cucurbitacin I), a selective janus kinase/signal transducer and activator of transcription 3 signaling pathway inhibitor with potent antitumor activity against human and murine cancer cells in mice," *Cancer Res*, 63:1270-1279, 2003.

(56) References Cited

OTHER PUBLICATIONS

Bollrath et al., "Gp130-mediated Stat3 activation in enterocytes regulates cell survival and cell-cycle progression during colitis-associated tumorigenesis," *Cancer Cell*, 15:91-102, 2009.
Boulton et al., "STAT3 activation by cytokines utilizing gp130 and related transducers involves a secondary modification requiring an H7-sensitive kinase," *Proc Natl Acad Sci USA*, 92(15):6915-6919, 1995.
Brierly et al., "IFNa/B: receptor interactions to biologic outcomes: understanding the circuitry," *J Interferon Cytokine Res*, 22:835-845, 2002.
Calzascia et al., "Homing phenotypes of tumor-specific CD8 T cells are predetermined at the tumor site by crosspresenting Apcs," *Immunity*, 22:175-184, 2005.
Carballido et al., "Interferon-alpha-2b enhances the natural killer activity of patients with transitional cell carcinoma of the bladder," *Cancer*, 72:1743-1748, 1993.
Chakraborty et al., "A novel Jak2/STAT3 pathway inhibitor promotes apoptosis and blocks growth of bladder cancer cells," *Proc $98_{th}$ Amer Assoc Cancer Res Annual Meeting*, Los Angeles, CA, 2007.
Chan et al., "Disruption of STAT3 reveals a critical role in both the initiation and the promotion stages of epithelial carcinogenesis," *J Clin Invest*, 114:720-728, 2004.
Chen et al., "Diversity and relatedness among the type I interferons," *J of Interferon Cytokine Res*, 24:687-698, 2004.
Chen et al., "Stat3 activation in human endometrial and cervical cancers," *Bri J Cancer*, 96:591-599, 2007.
Cortas et al., "Activation state EGFR and STAT3 as prognostic markers and resected non-small small lung cancer," *Lung Cancer*, 55:349-355, 2007.
Curiel et al., "Specific recruitment of regulatory T cells in ovarian carcinoma fosters immune privilege and predicts reduced survival," *Nat Med*, 10:942-949, 2004.
Database CA, Accession No. 446109, 1976.
De Simoni et al., "Central endotoxin induces different patterns of interleukin (IL)-1 beta and IL-6 messenger ribonucleic acid expression and IL-6 secretion in the brain and periphery," *Endocrinology*, 136:897-902, 1995.
Diefenbach et al., "Rael and H60 ligands of the NKG2D receptor stimulate tumour immunity," *Nature*, 413:165-171, 2001.
Domanski et al., "The type-1 interferon receptor. The long and short of it," *Cytokine Growth Factor Rev*, 7:143-151, 1996.
Dummer et al., "Randomized dose-escalation study evaluating peginterferon Alfa-2a in patients with metastatic malignant melanoma," *J Clin Oncol*, 24:1188-1194, 2006.
Extended European Search Report and Search Opinion issued in European Application No. 12162385.4, mailed Dec. 10, 2012.
Extended European Search Report and Search Opinion issued in European Application No. 12167605.0, mailed Jul. 4, 2012.
Fairclough et al., "Structure and rheology of aqueous gels," *Annu Rep Prog Chem, Sect C: Phys Chem*, 99:243-276, 2003.
Fecci et al., "Increased regulatory T-cell fraction amidst a diminished CD4 compartment explains cellular immune defects in patients with malignant glioma," *Cancer Res*, 66:3294-3302, 2006.
Fecci et al., "Systemic anti-CD25 monoclonal antibody administration safely enhances immunity in murine glioma without eliminating regulatory T cells," *Clin Cancer Res*, 12:4294-4305, 2006.
Fecci et al., "Systemic CTLA-4 blockade ameliorates glioma-induced changes to the CD4+ T cell compartment without affecting regulatory T-cell function," *Clin Cancer Res*, 13:2158-2167, 2007.
Ferrone et al., "Loss of HLA class I antigens by melanoma cells: molecular mechanisms, functional significance and clinical relevance," *Immunol Today*, 16:487-494, 1995.
Finnin et al., "Transdermal penetration enhancers: applications, limitations, and potential," *J Pharm Sci*, 88:955-958, 1999.
Fitzgerald et al., "Reactive glia are recruited by highly proliferative brain metastases of breast cancer and promote tumor cell colonization," *Clin Exp Metastasis*, 25:799-810, 2008.
Foley, "STAT3 regulates the generation of Th17 cells," *Sci STKE*, 2007.
Fontenot et al., "A well adapted regulatory contrivance: regulatory T cell development and the forkhead family transcription factor foxp3," *Nat Immunol*, 6:331-337, 2005.
Fujita et al , "Inhibition of STAT3 promotes the efficacy of adoptive transfer therapy using type-1 Ctls by modulation of the immunological microenvironment in a murine intracranial glioma," *J Immunol*, 180:2089-2098, 2008.
Gabrilovich et al., "Dendritic cells in antitumor immune responses. I. Defective antigen presentation in tumor-bearing hosts," *Cell Immunol*, 170:101-110, 1996.
Gabrilovich et al., "Vascular endothelial growth factor inhibits the development of dendritic cells and dramatically affects the differentiation of multiple hematopoietic lineages in vivo," *Blood*, 92:4150-4166, 1998.
Garrido et al., "Alterations of HLA class I expression in human melanoma xenografts in immunodeficient mice occur frequently and are associated with higher tumorigenicity," *Cancer Immunol Immunother*, Epub, 2009.
Gong et al., "Expression of activated signal transducer and activator of transcription 3 predicts expression of vascular endothelial growth factor in and angiogenic phenotype of human gastric cancer," *Clin Cancer Res*, 11:1386-1393, 2005.
Grace et al., "Structural and biologic characterization of pegylated recombinant IFN-a2b," *J Interferon and Cytokine Research*, 21:1103-1115, 2001.
Greiner et al., "Differential effects of recombinant human leukocyte interferons on cell surface antigen expression," *Cancer Res*, 46:4984-4990, 1986.
Grivennikov et al., "IL-6 and Stat3 are required for survival of intestinal epithelial cells and development of colitis-associated cancer," *Cancer Cell*, 15:103-113, 2009.
Guha et al., "WP1066, a potent inhibitor of Jak2/STAT3 pathway inhibits pancreatic tumor growth both in vitro and in vivo," *Proc $98^{th}$ Amer Assoc Cancer Res Annual Meeting*, Los Angeles, CA, 2007.
Halloran et al., "Regulation of MHC expression in vivo. II. IFN-A/B inducers and recombinant IFN-A modulate MHC antigen expression in mouse tissues," *J Immunol*, 142:4241-4247, 1989.
Haura et al., "Activated epidermal growth factor receptor-STAT3 signaling promotes tumor survival in vivo in non-small cell lung cancer," *Clin Cancer Res*, 11:8288-8294, 2005.
Heimans et al., "Treatment of leptomeningeal carcinomatosis with continuous intraventricular infusion of recombinant interleukin-2," *Surg Neurol*, 35:244-247, 1991.
Heimberger et al., "An epidermal growth factor receptor variant Iii peptide vaccination appears promising in newly diagnosed GBM patients: preliminary results of a randomized phase II clinical trial," *$74^{th}$ Annual Meeting of the American Association of Neurological Surgeons*, San Francisco, CA, 2006.
Heimberger et al., "Biological principles of brain tumor immunotherapy," in: Liau LM, et al., *Brain Tumor Immunotherapy* (Totowa, NJ, Humana Press Inc.), pp. 101-130, 2000.
Heimberger et al., "Bone marrow-derived dendritic cells pulsed with tumor homogenate induce immunity against syngeneic intracerebral glioma," *J Neuroimmunol*, 103:16-25, 2000.
Heimberger et al., "Dendritic cells pulsed with a tumor-specific peptide induce long-lasting immunity and are effective against murine intracerebral melanoma," *Neurosurgery*, 50:158-164, discussion 64-66, 2002.
Heimberger et al., "Epidermal growth factor receptor VIII peptide vaccination is efficacious against established intracerebral tumors," *Clin Cancer Res*, 9:4247-4254, 2003.
Heimberger et al., "Incidence and prognostic impact of Foxp3+ regulatory T cells in human gliomas," *Clin Cancer Res*, (In Press).
Heimberger et al., "Tumor-specific peptide vaccination in newly-diagnosed patients with GBM," *J Clin Oncol*, 24:Part 1, 2006.
Herrlinger et al., "Intrathecal treatment of C6 glioma leptomeningeal metastasis in wistar rats with interleukin-2," *J Neurooncol*, 27:193-203, 1996.
Hickey et al., "T-lymphocyte entry into the central nervous system," *J Neurosci Res*, 28:254-260, 1991.

(56) References Cited

OTHER PUBLICATIONS

Horiguchi et al., "Activation of signal transducer and activator of transcription 3 in renal cell carcinoma: a study of incidence and its association with pathological features and clinical outcome," *J Urology*, 168:762-765, 2002.
Hussain et al., "The role of human glioma-infiltrating microglia/macrophages in mediating antitumor immune responses," *Neuro Oncol*, 8:261-279, 2006.
Ito et al., "Differential regulation of human blood dendritic cell subsets by IFNs," *J Immunol*, 166:2961-2969, 2001.
Kaplan et al., "Nonparametric estimating from incomplete observations," *J Am Stat Assoc*, 53:457-481, 1958.
Kaser et al., "Interferon-alpha (IFN-A) enhances cytotoxicity in healthy volunteers and chronic hepatitis C infection mainly by the perforin pathway," *Clin Exp Immunol*, 118:71-77, 1999.
Keir et al., "IFN-α secretion by type 2 predendritic cells up-regulates MHC class I in the HIV-1-infected thymus," *J Immunol*, 168:325-331, 2002.
Khong et al., "Identification of multiple antigens recognized by tumor-infiltrating lymphocytes from a single patient: tumor escape by antigen loss and loss of MHC expression," *J Immunother*, 27:184-190, 2004.
Khoury et al., "Differential expression and clinical significance of tyrosine-phosphorylated STAT3 in ALK+ and ALK-anaplastic large cell lymphoma," *Clin Cancer Res*, 9:3692-3699, 2003.
Kim et al., "Adiponectin is a negative regulator of NK cell cytotoxicity," *J Immunol*, 176:5958-5964, 2006.
Kinjyo et al., "Loss of SOCS3 in T helper cells resulted in reduced immune responses and hyperproduction of interleukin 10 and transforming growth factor-B1," *J Exp Med*, 203:1021-1031, 2006.
Kirkwood et al., "High-dose interferon alpha-2b significantly prolongs relapse-free and overall survival compared with the GM2-KLH/QA-21 vaccine in patients with resected stage IIB-III melanoma: results of intergroup trial E1694/S9512/C509801," *Journal of Clinical Oncology*, 19:2370-2380, 2001.
Kolumam et al., "Type I interferons act directly on CD8 T cells to allow clonal expansion and memory formation in response to viral infection," *J Exp Med*, 202:637-650, 2005.
Kong et al., "A novel phosphorylated STAT3 inhibitor enhances T cell cytotoxicity against melanoma through inhibition of regulatory T cells," *Cancer Immunol. Immunother.*, 58:1023-1032, 2009.
Kong et al., "Antitumor activity and mechanism of action of a novel STAT3 inhibitor, WP1066, against human B-cell non-hodgkin's lymphoma and multiple myeloma," *Blood*, 106:429A, 1489, Part 1, 2005.
Kong et al, "Inhibition of p-STAT3 enhances IFN-A efficacy against metastatic melanoma in a murine model," *Clin Cancer Res*, 16:2550-2561, 2010.
Kortylewski et al , "Inhibiting Stat3 signaling in the hematopoietic system elicits multicomponent antitumor immunity," *Nat Med*, 11:1314-1321, 2005.
Kortylewski et al., "Regulation of the IL-23 and IL-12 balance by Stat3 signaling in the tumor microenvironment," *Cancer Cell*, 15:114-123, 2009.
Kortylewski et al., "Stat3 as a potential target for cancer immunotherapy," *J Immunother*, 30:131-139, 2007.
Krebs et al., "SOCS proteins: negative regulators of cytokine signaling," *Stem Cells*, 19:378387, 2001.
Kupferman et al, "A novel inhibitor of STAT3 signaling in head and neck squamous cell carcinoma," *Proc 97$^{th}$ Amer Assoc Cancer Res Annual Meeting*, Washington DC, 2006.
Kusuba et al., "Expression of p-STAT3 in human colorectal adenocarcinoma and adenoma; correlation with clinicopathological factors," *J Clin Pathol*, 58:833-838, 2005.
Lai et al., "Erythropoietin-medicated activation of Jak-Stat signaling contributes to cellular invasion in head and neck squamous cell carcinoma," *Oncogene*, 24:4442-4449, 2005.
Lang et al., "Shaping gene expression in activated and resting primary macrophages by IL-10," *J Immunol*, 169:2253-2263, 2002.

Lassmann et al., "STAT3 mRNA and protein expression in colorectal cancer: effects on STAT3-inducible targets linked to cell survival and proliferation," *J Clin Pathol*, 60:173179, 2007.
Lau et al., "Astrocytes produce and release interleukin-1, interleukin-6, tumor necrosis factor alpha and interferon-gamma following traumatic and metabolic injury," *J Neurotrauma*, 18:351-359, 2001.
Leaman et al., "Roles of JAKs in activation of STATs and stimulation of the c-fos gene expression by epidermal growth factor," *Mol Cell Biol*, 16(1):369-375, 1996.
Lee, "Role of NADPH oxidase-mediated generation of reactive oxygen species in the mechanism of apoptosis induced by phenolic acids in HepG2 human hepatoma cells," *Archives of Pharmacal Research*, 28(10):1183-1189, 2005.
Leong et al., "Targeted inhibition of Stat3 with a decoy oligonucleotide abrogates head and neck cancer cell growth," *Proc Natl Acad Sci USA*, 100:4138-4143, 2003.
Levitzki et al., "Tyrosine kinase inhibition: an approach to drug development," *Science*, 267:1782-1788, 1995.
Liang et al., "IFNa regulates NK cell cytotoxicity through STAT1 pathway," *Cytokine*, 23:190-199, 2003.
Lin et al., "STAT3 activation in macrophages following infection with salmonella," *Biochem Biophys Res Commun*, 321:828-834, 2004.
List et al., "Cytokine responses to intraventricular injection of interleukin 2 into patients with leptomeningeal carcinomatosis: rapid induction of tumor necrosis factor alpha, interleukin 1 beta, interleukin 6, gamma-interferon, and soluble interleukin 2 receptor (Mr 55,000 protein)," *Cancer Res*, 52:1123-1128, 1992.
Liu et al., "Hydrodynamics-based transfection in animals by systemic administration of plasmid DNA," *Gene Therapy*, 6:1258-1266, 1999.
Liyanage et al., "Prevalence of regulatory T cells is increased in peripheral blood and tumor microenvironment of patients with pancreas or breast adenocarcinoma," *J Immunol*, 169:2756-2761, 2002.
Madden et al., "The preclinical pharmacology of WP1066, a potent small molecule inhibitor of the JAK2/STAT3 pathway," *Proc 97$_{th}$ Amer Assoc Cancer Res Annual Meeting*, Washington DC, 2006.
Mantel, "Evaluation of survival data and two new rank order statistics arising in its consideration," *Cancer Chemother Rep*, 50:163-170, 1966.
Masamune et al., "Activation of JAK-STAT pathway is required for platelet-derived growth factor-induced proliferation of pancreatic stellate cells," *World J Gastroenterol*,11:3385-3391, 2005.
Masuda et al., "Constitutive activation of signal transducers and activators of transcription 3 correlates with cyclin dl overexpression and may provide a novel prognostic marker in head and neck squamous cell carcinoma," *Cancer Res*, 62:3351-3355, 2002.
Matyszek et al., "Miroglia induce myelin basic protein-specific T cell anergy or T cell activation, according to their state of activation," *Eur J Immunol*, 29:3063-3076, 1999.
McClusky et al., "Green chemistry approaches to the Knoevenagel condensation: comparison of ethanol, water, and solvent free (dry grind) approaches," *Tetrahedron Letters*, 43:3117-20, 2002.
Meinhold-Heerlein et al., "Molecular and prognostic distinction between serous ovarian carcinomas of varying grade and malignant potential," *Oncogene*, 24:1053-1065, 2005.
Meyers et al., "Neurotoxicity of intraventricularly administered alpha-interferon for leptomeningeal disease," *Cancer*, 68:88-92, 1991.
Mizoguchi et al., "Activation of STAT3, MAPK and AKT in malignant astrocytic gliomas: correlation with EGFR status, tumor grade, and survival," *J Neuropathol Exp Neurol*, 65:1181-1188, 2006.
Morford et al., "T cell receptor-mediated signaling is defective in T cells obtained from patients with primary intracranial tumors," *J Immunol*, 159:4415-4425, 1997.
Moser et al., "Biologic therapy for brain tumors," *Cancer Bull*, 42:117-126, 1991.
Nagaoka et al., "Selective antiproliferative activity of caffeic acid phenethyl ester analogues on highly liver-metastatic murine colon 26-L5 carcinoma cell line," *Bioorganic & Medicinal Chemistry*, 10:3351-3359, 2002.
Nefedova et al., "Activation of dendritic cells via inhibition of Jak2/STAT3 signaling," *J Immunol*, 175:4338-4346, 2005.

(56) References Cited

OTHER PUBLICATIONS

Nefedova et al., "Regulation of dendritic cell differentiation and antitumor immune response in cancer by pharmacologic-selective inhibition of the janus-activated kinase 2/signal transducers and activators of transcription 3 pathway," *Cancer Res*, 65:9525-9535, 2005.
O'Farrell et al., "IL-10 inhibits macrophage activation and proliferation by distinct signaling mechanisms: evidence for STAT3 dependent and independent pathways," *Embo J*, 17:1006-1018, 1998.
Obbens et al., "Phase I clinical trial of intralesional or intraventricular leukocyte interferon for intracranial malignancies," *J Neurooncol*, 3:61-67, 1985.
Office Action issued in Australian Application No. 2009268841, mailed Feb. 28, 2013.
Office Action issued in Canadian Application No. 2,548,152, mailed Oct. 16, 2012.
Office Action issued in Canadian Application No. 2,648,003, mailed Jul. 10, 2012.
Office Action issued in Chinese Application No. 200780019917.4, mailed Aug. 3, 2012, and English language translation thereof.
Office Action issued in Chinese Application No. 200980135799.2, issued Oct. 31, 2012 (and English language translation thereof).
Office Action issued in Eurasian Application No. 201170160, mailed May 12, 2012 (English language translation).
Office Action issued in European Application No. 09 794 969.7, mailed Mar. 8, 2013.
Office Action issued in Japanese Application No. 2009-503339, mailed Dec. 5, 2012, and English language translation thereof.
Office Action issued in Mexican Application No. MX/a/2008/012612, mailed Jan. 23, 2013.
Office Action issued in Philippines Application No. 1/2011/500038, issued Jan. 11, 2013.
Orsolic et al., "Effects of local administration of propolis and its polyphenolic compounds on tumor formation and growth," *Biological and Pharmaceutical Bulletin*, 28(10):1928-1933, 2005.
Palmer et al., "Interferon-Alpha (IFN-alpha) stimulates anti-melanoma cytotoxic T lymphocyte (CTL) generation in mixed lymphocyte tumour cultures (MLTC)," *Clin Exp Immunol*, 119:412-418, 2000.
Papadopoulos et al., "Intrathecal use of recombinant interleukin-2 (Ril-2) in the treatment of leptomeningeal disease (LMD) from metastatic melanoma," *Proc Annu Meet Am Soc Clin Oncol*, 14, 1995.
PCT International Preliminary Report on Patentability issued in International Application No. PCT/US2009/048782, issued Jan. 11, 2011.
PCT International Preliminary Report on Patentability issued in International Application.
PCT International Search Report issued in International Application No. PCT/US2010/059005, mailed Aug. 9, 2011.
PCT International Search Report issued in International Application No. PCT/US2009/048782, mailed Jan. 29, 2010.
PCT Written Opinion issued in International Application No. PCT/US2009/048782, mailed Jan. 29, 2010.
Pillemer et al., "Deficient SOCS3 expression in CD4+CD25+Foxp3+ regulatory T cells and SOCS3-mediated suppression of treg function," *Eur J Immunol*, 37:2082-2089, 2007.
Platten et al., "Malignant glioma biology: role for TGF-beta in growth, motility, angiogenesis, and immune escape," *Microsc Res Tech*, 52:401-410, 2001.
Priebe et al., "Design, synthesis and structure-activity relationships of novel Jak2/STAT3 signaling inhibitors," *Proc 97th Amer Assoc Cancer Res Annual Meeting*, Washington DC, 2006.
Qin et al., "Molecular mechanism of lipopolysaccharide-induced SOCS-3 gene expression in macrophages and microglia," *J Immunol*, 179:5966-5976, 2007.
Quadros et al., "Complex regulation of signal transducers and activators of transcription 3 activation in normal and malignant keratinocytes," *Cancer Res.*, 64:3934-3939, 2004.
Ravine et al., "Treatment with human recombinant leukocyte interferons inhibits in vitro invasive ability of human lung carcinoma cells," *Clin Exp Metastasis*, 4:191-203, 1986.

Rosenberg er al., "Cancer immunotherapy: moving beyond current vaccines," *Nat Med*, 10:909-915, 2004.
Roszman et al., "Modulation of T-cell function by gliomas," *Immunol Today*, 12:370-374, 1991.
Roszman et al., "Pokeweed mitogen-induced immunoglobulin secretion by peripheral blood lymphocytes from patients with primary intracranial tumors. Characterization of T helper and B cell function," *J Immunol*, 134:1545-1550, 1985.
Samanta et al., "Cross talk between Jak2 and Lyn in Bcr-Abl signaling pathway in cells from imatinib-sensitive and resistant chronic myelogenous leukemia (CML)," *Proc 98th Amer Assoc Cancer Res Annual Meeting*, Los Angeles, 2007.
Sampson et al., "Demographics, prognosis, and therapy in 702 patients with brain metastases from malignant melanoma," *J Neurosurg*, 88:11-20, 1998.
Sampson et al., "Temozolomide as a vaccine adjuvant in GBM," *J Clin Oncol*, 25(Supplement), No. 18S Part I of II:80s, 2007.
Schabet et al., "Intrathecal treatment of B16-F10 melanoma leptomeningeal metastasis (LM) in nude rats with MTX, ACNU or the combination of IFN-1 and TNF-A," *Brain Pathol*, 4:436, 1994.
Schaper et al., "Activation of the protein tyrosine phosphatase SHP2 via the interleukin-6 signal transducing receptor protein Gp130 requires tyrosine kinase Jak1 and limits acute-phase protein expression," *Biochemical Journal*, 335:557-565, 1998.
Schlette et al., "Survivin expression predicts poorer prognosis in anaplastic large-cell lymphoma," *J Clin Oncol*, 22:1682-1688, 2004.
Shah et al., "STAT3 expression in oral squamous cell carcinoma: association with clinicopathological parameters and survival," *Int J Biol Markers*, 21:175-183, 2006.
Shi et al., "Jsi-124 (cucurbitacin I) inhibits janus kinase-3/signal transducer and activator of transcription-3 signalling, downregulates nucleophosmin-anaplastic lymphoma kinase (ALK) and induces apoptosis in ALK-positive anaplastic large cell lymphoma cells," *Br J Haematol*, 135:26-32, 2006.
Shuai, "Regulation of cytokine signaling pathways by PIAS," *Proteins*, 16(2):196-202, 2006.
Siavash et al., "Abrogation of IL-6-mediated JAK signaling by the cyclopentenone prostaglandin 15d-PGJ(2) in oral squamous carcinoma cells," *Br J Cancer*, 91:1074-1080, 2004.
Siddiquee et al., "An oxazole-based small-molecule Stat3 inhibitor modulates STAT3 stability and processing and induces antitumor cell effects," *ACS Chemical Biology*, 787798, 2007.
Siddiquee et al., "Selective chemical probe inhibitor of STAT3, identified through structure-based virtual screening, induces antitumor activity," *Proc Natl Acad Sci USA*, 104:73917396, 2007.
Sikora et al., "IFN-A enhances peptide vaccine-induced CD8+ T cell numbers, effector function, and antitumor activity," *J Immunol*, 182:7398-7407, 2009.
Silva, "Role of stats as downstream signal transducers in Src family kinase-mediated tumorigenesis," *Oncogene*, 23(48):8017-8023, 2004.
Stark et al., "How cells respond to interferons," *Ann Rev Biochem*, 67:227-264, 1998.
Starr et al., "A family of cytokine-inducible inhibitors of signaling," *Nature*, 387:917-921, 1997.
Stofega et al., "Growth hormone regulation of SIRP and SHP-2 tyrosyl phosphorylation and association," *J Biol Chem*, 273:7112-7117, 1998.
Su et al., "Selective CD4+ lymphopenia in melanoma patients treated with temozolomide: a toxicity with therapeutic implications," *J Clin Oncol*, 22:610-616, 2004.
Supplementary European Search Report and Search Opinion issued European Application No. 09 79 4969, completed Mar. 9, 2012.
Tada et al., "Recent advances in immunobiology of brain tumors," *J. Neurooncol*, 17:261- 271, 1993.
Takeda et al., "Enhanced Th1 activity and development of chronic enterocolitis in mice devoid of Stat3 in macrophages and neutrophils," *Immunity*, 10:39-49, 1999.
Tang et al., "Effects of STAT3 antisense oligodeoxynucleotides on apoptosis and proliferation of mouse melanoma cell line B16," *Ai Zheng*, 25:269-274, 2006.
Tarkowski et al., "Early intrathecal production of interleukin-6 predicts the size of brain lesion in stroke," *Stroke*, 26:1393-1398, 1995.

(56) References Cited

OTHER PUBLICATIONS

Tirapu et al., "Low surface expression of B7-1 (CD80) is an immunoescape mechanism of colon carcinoma," *Cancer Res*, 66:2442-2450, 2006.

Turkson et al., "Phosphotyrosyl peptides block Stat3-mediated DNA binding activity, gene regulation, and cell transformation," *J Biol Chem*, 276:45443-45455, 2001.

Turkson et al., "STAT proteins: novel molecular targets for cancer drug discovery," *Oncogene*, 19:6613-6626, 2000.

Van Wagoner et al., "Interleukin-6 (IL-6) production by astrocytes: autocrine regulation by IL-6 and the soluble IL-6 receptor," *J. Neurosci*, 19:5236-5244, 1999.

Voigt et al., "CD28-mediated costimulation impacts on the differentiation of DC vaccination-induced T cell responses," *Clin Exp Immunol*, 143:93-102, 2006.

Wang et al., "Effects of high-dose IFNa2b on regional lymph node metastases of human melanoma: modulation of STAT5, FOXP3, and IL-17," *Clin Cancer Res*, 14:8314-8320, 2008.

Wang et al., "IL-17 can promote tumor growth through an IL-6 Stat3 signaling pathway," *J Exp Med* 206:1457-1464, 2009.

Winston et al., "JAK2, Ras and Raf are required for activation of extracellular signal-regulated kinase/mitogen-activated protein kinase by growth hormone," *J Biol Chem*, 270:30837-30840, 1995.

Wylie et al., "Carboxylated histidine is a pH-dependent product of pegylation with SC-PEG," *Pharmaceutical Research*, 18:1354-1360, 2001.

Xi et al., "In vivo antitumor efficacy of STAT3 blockade using a transcription factor decoy approach: implications for cancer therapy," *Oncogene*, 24:970-979, 2005.

Yang et al., "Altered p-STAT3 (Tyr705) expression is associated with histological grading and intratumour microvessel density in hepatocellular carcinoma," *J Clin Pathol*, 60:642648, 2007.

Yang et al., "STAT3 regulates cytokine-mediated generation of inflammatory helper T cells," *J Biol Chem*, 282:9358-9363, 2007.

Yang et al., "The role of p-STAT3 (ser727) revealed by its association with Ki-67 in cervical intraepithelial neoplasia," *Gynecologic Oncol*, 98:446-452, 2005.

Yi-qun et al., "B7-blocking agents, alone or in combination with cyclosporine A, induce antigen-specific anergy of human memory T cells," *J Immunol*, 158:4734-4740, 1997.

Yoshimura et al., "SOCS proteins, cytokine signaling and immune regulation," *Nat Rev Immunol*, 7:454-465, 2007.

Yu et al., "Crosstalk between cancer and immune cells: role of STAT3 in the tumour microenvironment," *Nat Rev Immunol*, 7:41-51, 2007.

Yu et al., "STATs in cancer inflammation and immunity a leading role for STAT3," *Nature*, 9:798-809, 2009.

Yuan et al., "Central role of the threonine residue within the p_1 loop of receptor tyrosine kinase in STAT3 constitutive phosphorylation in metastatic cancer cells," *Mol Cell Biol*, 24(21):9390-9400, 2004.

Zorn et al., "IL-2 regulates FOXP3 expression in human CD4+CD25+ regulatory T cells through a STAT-dependent mechanism and induces the expansion of these cells in vivo," *Blood*, 108:1571-1579, 2006.

Zoumbos et al., "Interferon is a mediator of hematopoietic suppression in aplastic anemia in vitro and possibly in vivo," *Proc Natl Acad Sci USA*, 82:188-192, 1985.

\* cited by examiner

U87 Ex. 2/4 Dose Response

INHIBITORS OF PROLIFERATION AND ACTIVATION OF SIGNAL TRANSDUCER AND ACTIVATORS OF TRANSCRIPTION (STATS)

CROSS-REFERENCE TO RELATED APPLICATIONS

This is application is a continuation application of U.S. application Ser. No. 12/989,944, which was the National Stage of international Application No. PCT/US09/48782, filed Jun. 26, 2009, which claims the benefit of U.S. Provisional Application Ser. No. 61/079,002 filed on Jul. 8, 2008. The application is incorporated by reference herein in its entirety.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

FIELD OF THE INVENTION

Pyridine compounds and compositions and their application as pharmaceuticals for the treatment of disease are provided herein. Methods of inhibiting of STAT3 and/or STAT5 activation in a human or animal subject are also provided for the treatment of diseases such as cancer.

BACKGROUND OF THE INVENTION

The Jak/STAT signaling pathway is known to be activated in a number of cancers and inflammatory diseases. When activated through phosphorylation of a single tyrosine residue STAT3 dimerizes, translocates to nucleus, and serves as a transcription factor driving the upregulation of a number of proliferative and pro-survival genes including survivin, VEGF, Bcl-2, and Bcl-xL. These gene products are known to promote the growth and metastasis of over 20 tumor types and are also associated with the promotion of several proliferative skin disorders including psoriasis, T-cell lymphoma, and atopic dermatitis.

Inhibition of STAT3 phosphorylation in tumor bearing animals leads to the induction of apoptotic cell death and in preclinical orthotopic models of several diseases a significant reduction in tumor size. Likewise in inflammatory skin diseases inhibition of STAT3 phosphorylation leads to resolution of plaques, scales, and other associated lesions.

While the development of inhibitors of this pathway is currently desirable, a variety of inhibition (such as small molecule, antisense, iRNA) approaches have been tried with unsatisfactory results.

SUMMARY OF THE INVENTION

Novel pyridine compounds and pharmaceutical compositions that inhibit cancer, have been found, together with methods of synthesizing and using the compounds including methods for the treatment of STAT3-mediated diseases and conditions in a patient by administering the compounds. The compounds can also be useful in treating STAT5-mediated diseases and conditions. This class of compounds is defined by structural Formula I as follows:

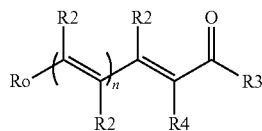

or a pharmaceutically acceptable salt or solvate thereof, wherein:

n is an integer selected from 1, 2 or 3;

$R_0$ is $R_1$, or $R_0$ is $R_1$—$Z_1$— wherein $Z_1$ is alkyl, and specifically may be a lower alkyl such as —$(CH_2)_{m3}$— where $m_3=0, 1, 2, 3,$ or 4;

$R_1$ is:

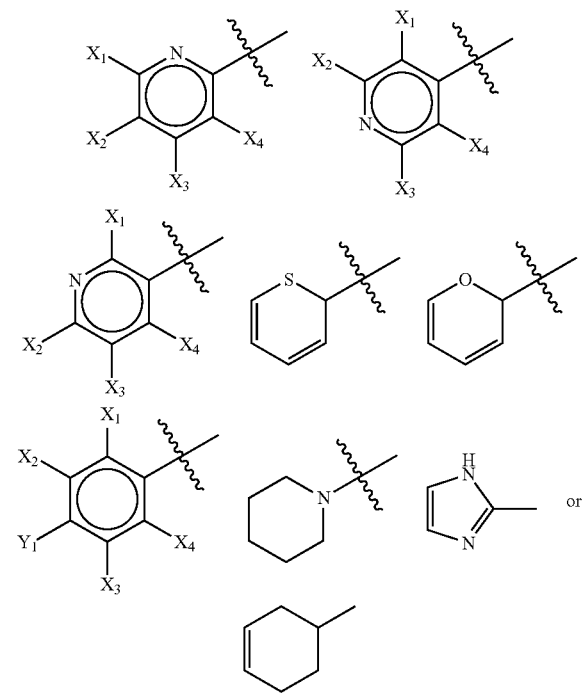

wherein $X_1, X_2, X_3,$ and $X_4$, are each independently hydrogen, halogen, alkyl, alkoxy, OH, trihalomethyl, or $NO_2$, and $Y_1$ is OH, halogen, specifically including Br and Cl, or $O_2N$;

$R_2$ is alkyl, alkenyl, alkynyl, alkoxy, alkylaryl, halogen, hydrogen, OH, $NO_2$, thioether, amine, SH, or $NH_2$;

$R_3$ is;

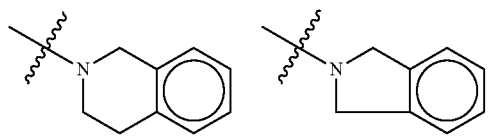

-continued

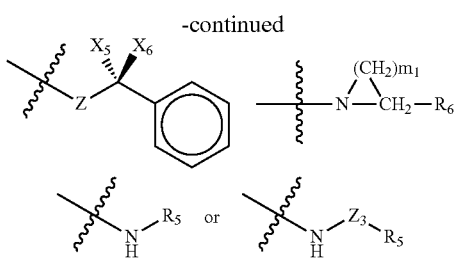

wherein $m_1$ is an integer selected from 1, 2, 3, or 4, $X_5$ and $X_6$ are each independently hydrogen, alkyl, upper alkyl, lower alkyl, aryl, alkoxyl, aryloxyl, cyclic alkyl, cycloalkyl, cycloarylalkyl, aralkyl, alkylester, alkylester-alkyl, alkylacetoxyl, hydroxyl, hydroxylalkyl, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, or cyclohexyl, Z is NH, S, or O, and $Z_3$ is alkyl or lower alkyl;

$R_4$ is CN, substituted amine, $CH_2$S-alkyl, alkyl, or $CH_2N_3$; and $R_5$ and $R_6$ are each independently selected from the group consisting of:

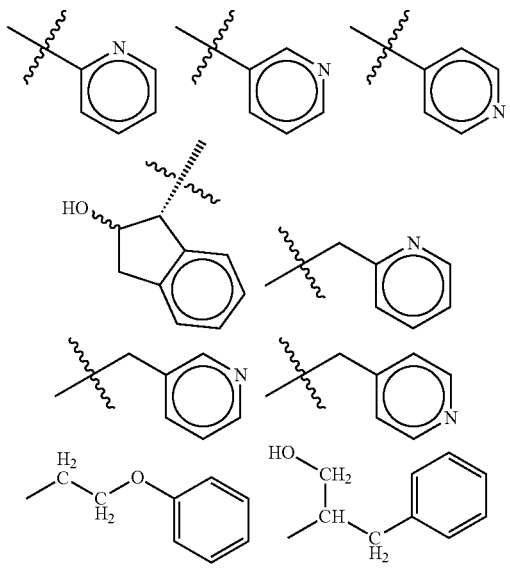

monosaccharide (e.g., glucose, fructose, galactose, etc.), polysaccharide, monosaccharide derivative (e.g., an acetylated monosaccharide such as acetylated galactose, 1,2,3,4-diisopropylideno-D-g-alactose) substituted and unsubstituted aryl, and substituted and unsubstituted alkylaryl.

The compounds described herein possess useful STAT3 inhibiting activity, and may be used in the treatment or prophylaxis of a disease or condition in which STAT3 plays an active role. Thus, in broad aspect, pharmaceutical compositions comprising one or more compounds of the present invention together with a pharmaceutically acceptable carrier, as well as methods of making and using the compounds and compositions is described.

Methods for inhibiting STAT3 or STAT5 activation are also provided herein. Methods for treating a STAT3-mediated or STAT5-mediated disorder in a patient in need of such treatment comprising administering to said patient a therapeutically effective amount of a compound or composition described herein. Further, these compounds presented herein can be used in the manufacture of a medicament for the treatment of a disease or condition ameliorated by the modulation of STAT3 or STAT5 activation.

BRIEF DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof reference is now made to the following descriptions taken in conjunction with the accompanying drawings, in which.

DETAILED DESCRIPTION

Figure 1:
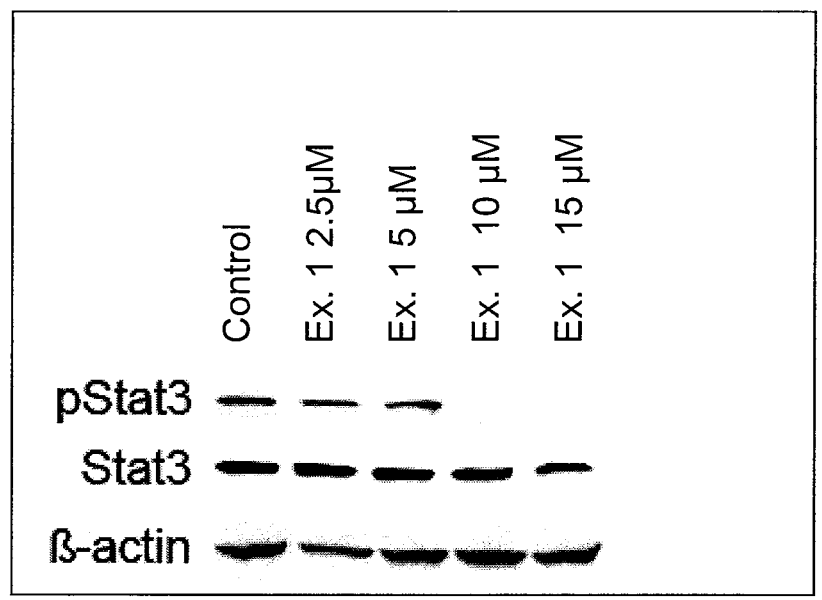
FIG. 1 is data from experimentation that shows the inhibition of STAT3 phosphorylation by the compound of Example 1 in Colo357FG tumor cell line.
Figure 2:
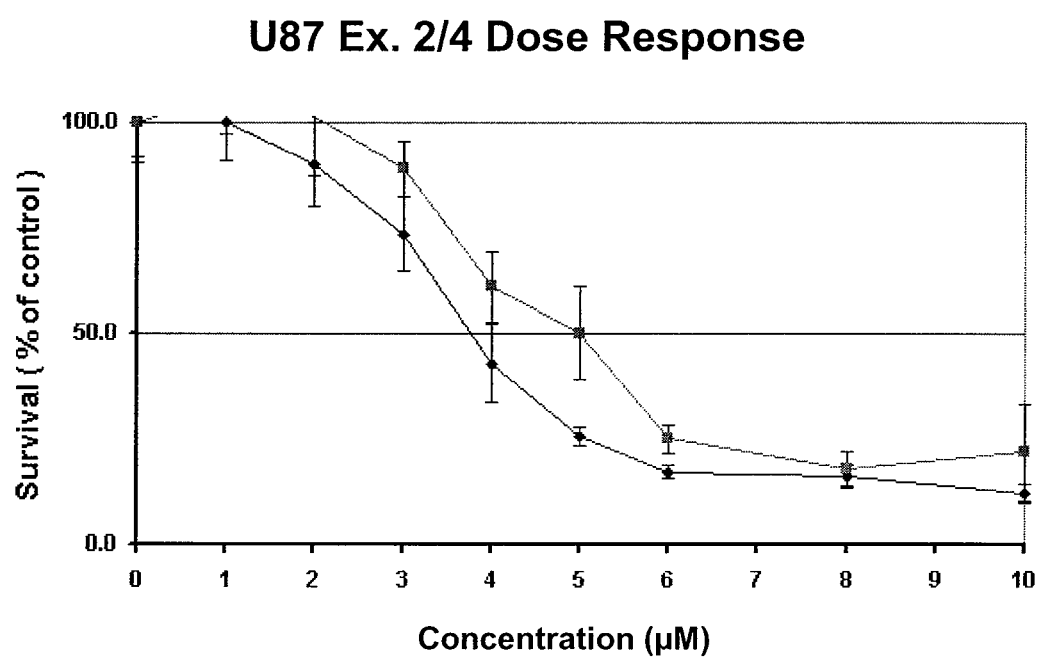
FIG. 2 provides a chart of the data show the lack of cell survival of the U87 brain tumor after administration of the compounds of Example 2 and Example 4.
Figure 3:
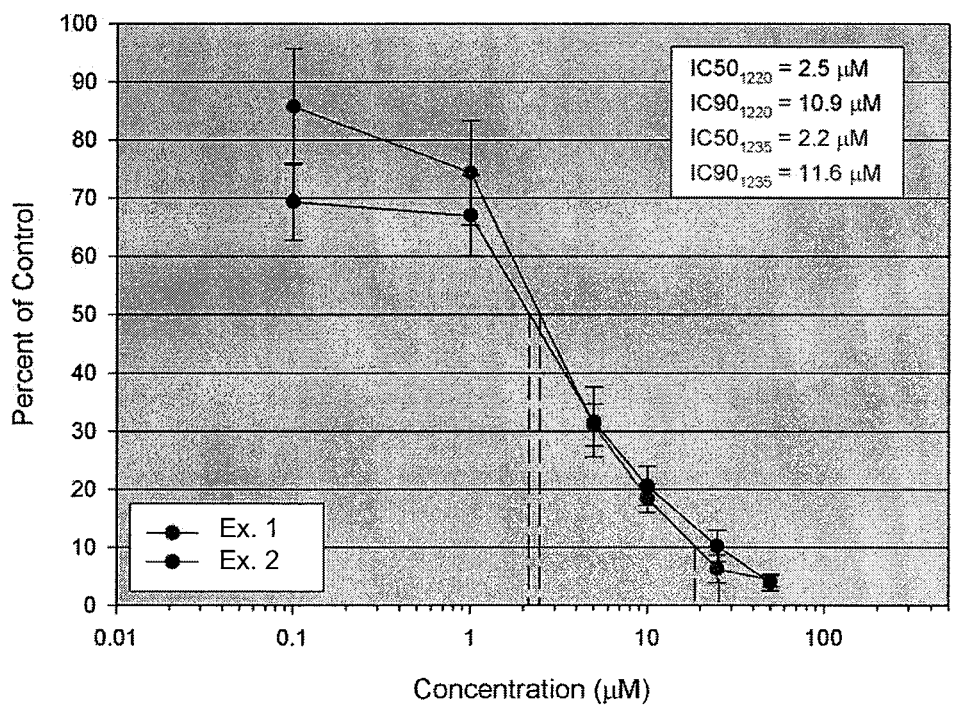
FIG. 3 depicts the data depicting the inhibition of the SCOVE3 ovarian cancer cell growth after administration of the compounds of Example 2 and Example 4.
Figure 4:
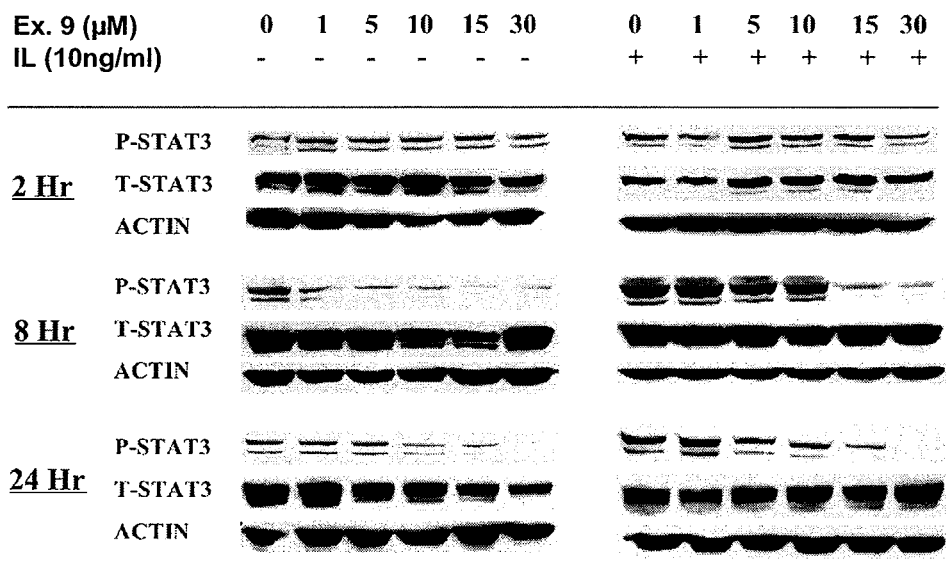
FIG. 4 is data from the compound of Example 9 constitutively inhibiting the IL-2 phosphorylation of STAT-3 in D54 brain tumor cell lines.

Compounds presented herein have the general Formula I:

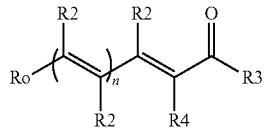

or a pharmaceutically acceptable salt or solvate thereof, wherein:

n is an integer selected from 1, 2 or 3;

$R_0$ is $R_1$, or $R_0$ is $R_1$—$Z_1$— wherein $Z_1$ is alkyl, and specifically may be a lower alkyl such as —$(CH_2)_{m3}$— where $m_3$=0, 1, 2, 3, or 4;

$R_1$ is:

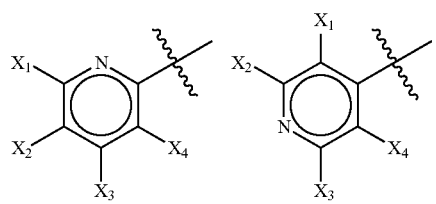

-continued

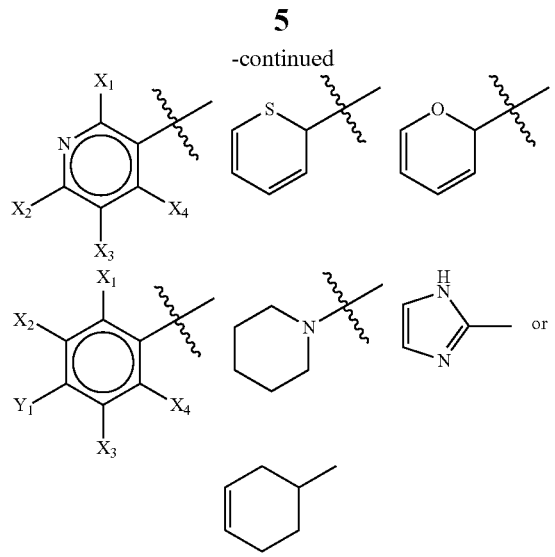

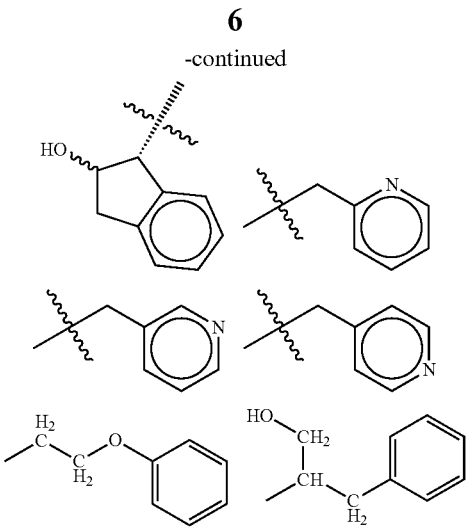

wherein $X_1$, $X_2$, $X_3$, and $X_4$, are each independently hydrogen, halogen, alkyl, alkoxy, OH, trihalomethyl, or $NO_2$, and $Y_1$ is OH, halogen, specifically including Br and Cl, or $O_2N$;

$R_2$ is alkyl, alkenyl, alkynyl, alkoxy, alkylaryl, halogen, hydrogen, OH, $NO_2$, thioether, amine, SH, or $NH_2$;

$R_3$ is:

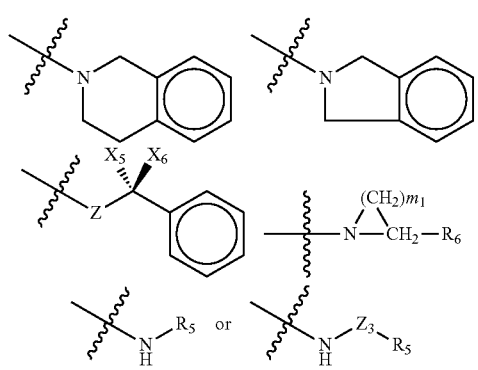

wherein $m_1$ is an integer selected from 1, 2, 3, or 4, $X_5$ and $X_6$ are each independently hydrogen, alkyl, upper alkyl, lower alkyl, aryl, alkoxyl, aryloxyl, cyclic alkyl, cycloalkyl, cycloarylalkyl, aralkyl, alkylester, alkylesteralkyl, alkylacetoxyl, hydroxyl, hydroxylalkyl, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, or cyclohexyl, Z is NH, S, or O, and $Z_3$ is alkyl or lower alkyl;

$R_4$ is CN, substituted amine, $CH_2S$-alkyl, alkyl, or $CH_2N_3$; and $R_5$ and $R_6$ are each independently selected from the group consisting of:

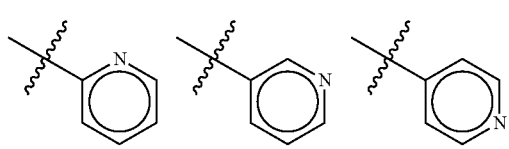

monosaccharide (e.g., glucose, fructose, galactose, etc.), polysaccharide, monosaccharide derivative (e.g., an acetylated monosaccharide such as acetylated galactose, 1,2,3,4-diisopropylideno-D-g-alactose) substituted and unsubstituted aryl, and substituted and unsubstituted alkylaryl.

More specifically, $R_5$ may be an alkylaryl having the structure:

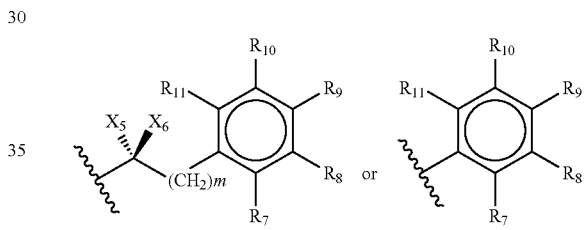

wherein m is an integer selected from 0, 1, 2, 3, 4, 5, 6, or 7, $X_5$ and $X_6$ are each independently hydrogen, alkyl, upper alkyl, lower alkyl, aryl, alkoxyl, aryloxyl, cyclic alkyl, cycloalkyl, cycloarylalkyl, aralkyl, alkylester, alkylesteralkyl, alkylacetoxyl, hydroxyl, hydroxylalkyl, cyclopropyl, cyclobutyl, —$CH_3$, —$CH_2OH$, cyclopentyl, —$CH_2OAc$, —$CH_2OC(O)C(CH_3)_3$, —$CH_2C_6H_5$, or cyclohexyl, and $R_7$, $R_8$, $R_9$, $R_{10}$, and $R_{11}$, are each independently selected from the group consisting of hydrogen, halogen, alkyl, alkoxy, OH, trihalomethyl, and $NO_2$.

Even more specifically, $R_5$ can be any one of the following:

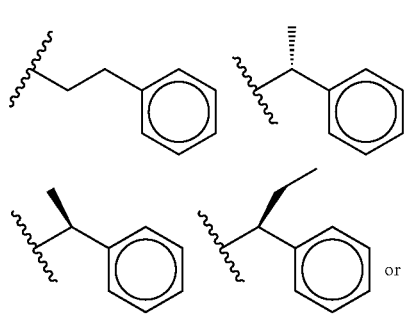

-continued

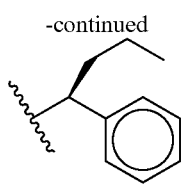

Furthermore, in Formula I, $R_1$ may be specifically:

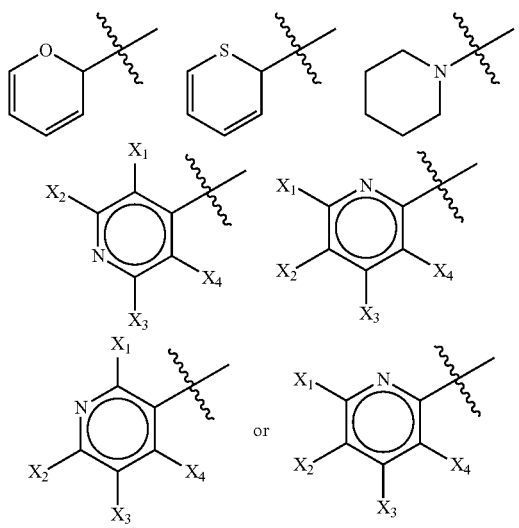

wherein $X_1$ may be a halogen such as Br or Cl, and $X_2$, $X_3$, and $X_4$, are each independently hydrogen, halogen, alkyl, alkoxy, OH, trihalomethyl, or $NO_2$.

As used herein, the terms below have the meanings indicated.

As used herein, the term "amino" means —$NH_2$; the term "nitro" means —$NO_2$; the term "halo" designates —F, —Cl, —Br or —I; the term "mercapto" means —SH; the term "cyano" means —CN; the term "silyl" means —$SiH_3$, and the term "hydroxy" means —OH.

An "amide" refers to a —C(O)—NH—R, where R is either alkyl, aryl, alkylaryl, or hydrogen.

A "thioamide" refers to a —C(S)—NH—R, where R is either alkyl, aryl, alkylaryl, or hydrogen.

An "ester" refers to a —C(O)—OR', where R' is either alkyl, aryl, or alkylaryl.

An "amine" refers to a N(R")R'", where R" and R'" is each independently either hydrogen, alkyl, aryl, or alkylaryl, provided that R" and R'" are not both hydrogen.

A "thioether" refers to —S—R, where R is either alkyl, aryl, or alkylaryl,

A "sulfonyl" refers to $S(O)_2$—R, where R is aryl, C(CN) =C-aryl, $CH_2$—CN, alkylaryl, NH-alkyl, NH-alkylaryl, or NH-aryl.

An "alkane" refers to an acyclic branched or unbranched hydrocarbon, in many cases having the general formula $C_nH_{2n+2}$.

An "alkyl" refers to a univalent group derived from an alkane by removal of a hydrogen atom from any carbon atom thus having the formula —$C_nH_{2n+1}$ in many cases. Alkyl groups include either straight-chained or branched chained and/or groups that may be substituted with additional acyclic alkyl, cycloalkyl, or cyclic alkyl groups. An alkyl group may be heteroatom-substituted or heteroatom-unsubstituted, see below. Preferably, an alkyl group has to 12 carbons and may be referred to as a lower alkyl when having 1 to 7 carbons, and/or an upper alkyl when having 8 or more carbon atoms. Alkyl further refers and includes a "divalent alkyl" that refers to a divalent group derived from an alkane by removal of two hydrogen atoms from either the same carbon atom (e.g. methylene, ethylidene, propylidene) or from different carbon atoms (e.g. —$C_2H_4$—).

A "cycloalkane" refers to saturated monocyclic hydrocarbons with or without side chains.

A "cycloalkyl" specifically refers to a univalent group derived from cycloalkane by removal of a hydrogen atom from a ring carbon atom.

A cyclic alkyl and/or alkyl cyclic or alicyclic compound refers to an aliphatic compound having a carbocyclic ring structure that may be saturated or unsaturated, but are not a benzenoid or other aromatic system, and where the univalent group is derived by removal of a hydrogen atom from any carbon of alkane chain.

The term "heteroatom-substituted," when used to modify a class of organic radicals (e.g. alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —$NO_2$, —$N(CH_3)_2$, amino, or —SH. Specific heteroatom-substituted organic radicals are defined more fully below.

The term "heteroatom-unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —$C_6H_4C\equiv CH$ is an example of a heteroatom-unsubstituted aryl group, while —$C_6H_4F$ is an example of a heteroatom-substituted aryl group. Specific heteroatom-unsubstituted organic radicals are defined more fully below.

The term "heteroatom-unsubstituted $C_n$-alkyl" refers to an alkyl, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$, cyclopropylmethyl, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, and —$CH_2C(CH_3)_3$ are all examples of heteroatom-unsubstituted alkyl groups.

The term "heteroatom-substituted $C_n$-alkyl" refers to an alkyl, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$Cl_2Cl$, —$Cl_2Br$, —$CH_2OCH_3$, —$CH_2OCH_2CH_3$, —$CH_2OCH_2CH_2CH_3$, —$CH_2OCH(CH_3)_2$, $CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2OCH(CH_2)_2$, —$CH_2NHCH(CH_2)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_1$, —CH$_2$CH$_2$NHCH$_2$CH$_2$CH$_3$, —CH$_2$CH$_2$NHCH(CH$_3$)$_2$, —CH$_2$CH$_2$N(CH$_2$CH$_3$)$_2$, —CH$_2$CH$_2$NHCO$_2$C(CH$_3$)$_3$, and —CH$_2$Si(CH$_3$)$_3$.

The term "heteroatom-unsubstituted C$_n$-cycloalkyl" refers to a cycloalkyl, further having a total of n carbon atoms, all of which are nonaromatic, 3 or more hydrogen atoms, and no heteroatoms. For example, a heteroatom-unsubstituted C$_1$-C$_{10}$-cycloalkyl has 1 to 10 carbon atoms. The groups —CH(CH$_2$)$_2$ (cyclopropyl), cyclobutyl, cyclopentyl, and cyclohexyl, are all examples of heteroatom-unsubstituted cycloalkyl groups.

The term "heteroatom-substituted C$_n$-cycloalkyl" refers to a cycloalkyl, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C$_1$-C$_{10}$-cycloalkyl has 1 to 10 carbon atoms.

An "alkenyl" group refers to an unsaturated hydrocarbon group containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted, the substituted group(s) is preferably hydroxyl, cyano, alkoxy, =O, =S, NO$_2$, N(CH$_3$)$_2$, halogen, amino, or SH.

The term "heteroatom-unsubstituted C$_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted C$_2$-C$_{10}$-alkenyl has 2 to 10 carbon atoms. Heteroatom-unsubstituted alkenyl groups include: —CH=CH$_2$, —CH=CHCH$_3$, —CH=CHCH$_2$CH$_3$, —CH=CHCH$_2$CH$_2$CH$_3$, —CH=CHCH(CH$_3$)$_2$, —CH=CHCH(C$_2$)$_2$, —CH$_2$CH=CH$_2$, —CH$_2$CH=CHCH$_3$, —CH$_2$CH=CHCH$_2$CH$_3$, —CH$_2$CH=CHCH$_2$CH$_2$CH$_3$, —CH$_2$CH=CHCH(CH$_3$)$_2$, —CH$_2$CH=CHCH(CH$_2$)$_2$, and —CH=CH—C$_6$H$_5$.

The term "heteroatom-substituted C$_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, u heteroatom-substituted C$_2$-C$_{10}$-alkenyl has 2 to 10 carbon atoms. The groups, —CH=CHF, —CH=CHCl and —CH=CHBr, are examples of heteroatom-substituted alkenyl groups.

An "alkynyl" group refers to an unsaturated hydrocarbon group containing at least one carbon-carbon triple bond, including straight-chain, branched chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted, the substituted group(s) is preferably hydroxyl, cyano, alkoxy, =O, =S, NO$_2$, N(CH$_3$)$_2$, amino, or SH.

The term "heteroatom-unsubstituted C$_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted C$_2$-C$_{10}$-alkynyl has 2 to 10 carbon atoms. The groups, —C≡CH, —C≡CCH$_3$, and —C≡CC$_6$H$_5$ are examples of heteroatom-unsubstituted alkynyl groups.

The term "heteroatom-substituted C$_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C$_2$-C$_{10}$-alkynyl has 2 to 10 carbon atoms. The group, —C≡CSi(CH$_3$)$_3$, is an example of a heteroatom-substituted alkynyl group.

An "aryl" group refers to an aromatic group which has at least one ring having a conjugated pi electron system, and includes carbocyclic aryl, heterocyclic aryl, and biaryl groups, all of which may be optionally substituted. Preferably, the aryl is a substituted or unsubstituted phenyl or pyridyl. Preferred aryl substituent(s) are halogen, trihalomethyl, hydroxyl, SH, NO$_2$, amine, thioether, cyano, alkoxy, alkyl, and amino groups.

An "alkylaryl" group refers to an alkyl (as described above), covalently joined to an aryl group (as described above). Preferably, the alkyl is a lower alkyl.

"Carbocyclic aryl" groups are groups wherein the ring atoms on the aromatic ring are all carbon atoms. The carbon atoms are optionally substituted with preferred groups as described for aryl groups above.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, N-lower alkyl pyrrolo, pyrimidyl, pyrazinyl, imidazoyl, and the like, all optionally substituted.

The term "heteroatom-unsubstituted C$_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C$_6$-C$_{10}$-aryl has 6 to 10 carbon atoms. Examples of heteroatom-unsubstituted aryl groups include phenyl, methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$=CH(CH$_2$)$_2$, —Cl$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, quinolyl, indolyl, and the radical derived from biphenyl. The term "heteroatom-unsubstituted aryl" includes carbocyclic aryl groups, biaryl groups, and radicals derived from polycyclic fused hydrocarbons (PAHs).

The term "heteroatom-substituted C$_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C$_1$-C$_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —C$_6$H$_4$F, —C$_6$H$_4$Cl, —C$_6$H$_4$Br, C$_6$H$_4$I, —C$_6$H$_4$OH, —C$_5$H$_4$OCH$_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4CH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH=CH_2$, —$C_6H_4CF_3$, —$C_6H_4CN$, —$C_6H_4C-CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCHCH_3$, —$C_6H_4CON(CH_3)_2$, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated in an aromatic ring structure, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —$COCH_3$, —$COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2C_{13}$, —$COC_6H_4CH(CH_3)_2$, —$COC_6H_4CH(CH_2)_2$, and —$COC_6H_3(CH_3)_2$, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P. and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples heteroatom-substituted acyl groups.

An "alkoxy" group refers to an "—O-alkyl" group, where "alkyl" is defined above.

An "aryl" group refers to an aromatic group which has at least one ring having a conjugated pi electron system, and includes carbocyclic aryl, heterocyclic aryl, and biaryl groups, all of which may be optionally substituted. Preferably, the aryl is a substituted or unsubstituted phenyl or pyridyl. Preferred aryl substituent(s) are halogen, trihalomethyl, hydroxyl, SH, OH, $NO_2$, amine, thioether, cyano, alkoxy, alkyl, and amino groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —$OCH_3$, —$OCH_2CH_3$, —$OCH_2CH_3$, —$OCH(CH_3)_2$, and —$OCH(CH_2)_2$.

The term "heteroatom-substituted $C_n$-alkoxy" refers to a group, having the structure —OR, in which R is a heteroatom-substituted $C_n$-alkyl, as that term is defined above. For example, —$OCH_2CF_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above.

The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above.

The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted. $C_n$-aryl, as that term is defined above. An example of a heteroatom-unsubstituted aryloxy group is —$OC_6H_5$.

The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —$OCOCH_3$ is an example of a heteroatom-unsubstituted acyloxy group.

The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted. $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atom, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl (alkynyl)amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P. and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P. and S. For example, a heteroatom-substituted $C_7$-$C_{10}$-aralkylamino has 7 to 10 carbon atoms. The term "heteroatom-substituted $C_n$-aralkylamino" includes groups, having the structure which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted as that term is defined above. The term amido includes N-alkyl-amido, N-arylamido, N-aralkyl-amido, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I. Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

The term "heteroatom-unsubstituted $C_n$-sulfonamido" refers to a radical, having a single nitrogen atom as the point of attachment, further having a sulfonyl group attached via its sulfur atom to the nitrogen atom, further having a linear or branched, cyclic or acyclic structure, further having a total of n carbon atoms, I or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term amido includes N-alkyl-sulfonamido, N-aryl-sulfonamido, N-aralkyl-sulfonamido, sulfonylamino, alkylsulfonamino, and arylsulfonamino groups. The group, —NHS(O)$_2$CH, is an example of a heteroatom-unsubstituted sulfonamide group.

The term "heteroatom-substituted $C_n$-sulfonamido" refers to a radical, having a single nitrogen atom as the point of attachment, further having a sulfonyl group attached via its sulfur atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the sulfur and oxygen atoms of the sulfonyl group, wherein each additional heteroatom is independently selected from the group consisting of N, O, F, Cl, Br, I, Si, F, and S. For example, a heteroatom-substituted sulfonamido has 1 to 10 carbon atoms. The group, —NHS(O)$_2$OCH$_3$, is an example of a heteroatom-substituted sulfonamido group.

The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group.

The term "heteroatom-substituted $C_n$-alkylthio" refers to a group, having the structure —SR, in Which R is a heteroatom-substituted. $C_n$-alkyl, as that term is defined above.

The term "heteroatom-unsubstituted enylthio" refers to a group, having the structure —SR, in which R is a heteroatom-unsubstituted $C_n$-alkenyl, as that term is defined above.

The term "heteroatom-substituted $C_n$-alkenylthio" refers to a group, having the structure —SR, in which R is a heteroatom-substituted $C_n$-alkenyl, as that term is defined, above.

The term "heteroatom-unsubstituted $C_n$-alkynylthio" refers to a group, having the structure —SR, in which R is a heteroatom-unsubstituted $C_n$-alkynyl, as that term is defined above.

The term "heteroatom-substituted $C_n$-alkynylthio" refers to a group, having the structure —SR, in which R is a heteroatom-substituted $C_n$-alkynyl, as that term is defined above.

The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group.

The term "heteroatom-substituted $C_n$-arylthio" refers to a group, having the structure —SAr, in which Ar is a heteroatom-substituted. $C_n$-aryl, as that term is defined above.

The term "heteroatom-unsubstituted. $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group.

The term "heteroatom-substituted $C_n$-aralkylthio" refers to a group, having the structure —SAr, in which Ar is a heteroatom-substituted $C_n$-aralkyl, as that term is defined above.

The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group.

The term "heteroatom-substituted $C_n$-acylthio" refers to a group, having the structure —SAc, in which Ac is a heteroatom-substituted $C_n$-acyl, as that term is defined above.

The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —Si(CH$_3$); and Si(CH$_3$)$_2$C(CH$_3$)$_3$, are examples of heteroatom-unsubstituted alkylsilyl groups.

The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook (2002), which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "$IC_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein the specification, "a" or "an" may mean one or more. As used herein in the claim(s), when used in conjunction with the word "comprising" or "having," the words "a" or "an" may mean one or more than one. As used herein "another" may mean at least a second or more.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-$\beta$, transforming growth factor-$\beta$; IFN-$\gamma$, interferon-$\gamma$; LPS, bacterial endotoxic lipopolysaccharide; TNF-$\alpha$, tumor necrosis factor-$\alpha$; IL-1$\beta$, interleukin-1$\beta$; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds provided herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrags of the compounds as described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug.

Furthermore, a wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately brining into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soil capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Preferred unit dosage formulations are those containing an effective dose, as herein below recited, or an appropriate fraction thereof, of the active ingredient.

It should be understood that in addition to the ingredients particularly mentioned above, the formulations may include other agents conventional in the art having regard to the type of formulation in question, for example those suitable for oral administration may include flavoring agents.

The compounds provided herein can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In short, the compounds of the invention may be administered orally, topically, or by injection at a dose of from 0.1 to 500 mg/kg per day. Tablets or other forms of presentation provided in discrete units may conveniently contain an amount of compound of the invention which is effective at such dosage or as a multiple of the same, for instance, units containing 5 mg to 500 mg.

The amount of active ingredient that may be combined with the carrier materials to produce a single dosage form will vary depending upon the host treated and the particular mode of administration.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound provided herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, methods for treating STAT3-mediated disorders or conditions (as well as STAT5-mediated disorders or conditions) in a human or animal subject in need of such treatment comprise administering to the subject an amount of a compound presented herein effective to reduce or prevent said disorder in the subject in combination with at least one additional agent for the treatment of said disorder that is known in the art. In a related aspect, therapeutic compositions comprise at least one these compounds in combination with one or more additional agents for the treatment of STAT3- and STAT5-mediated disorders.

The compounds described herein may be useful for the treatment of a wide variety of disorders or conditions where inhibition or modulation of the STAT3 pathway is needed. The compounds decrease and can therapeutically treat proliferative disease conditions, Uses for these compounds include the compounds as agents to: decrease STAT3 activity; STAT3 phosphorylation; and the expression of proteins controlled by transcriptional activation by activated STAT3, Along these lines, the compounds can be specifically used as agents to decrease VEGF, MMP9, MMP2, survivin, c-Myc, MMP-1, MEK-5, c-FOS, 1 COX-2, Bcl-xl, MMP-10, HSP-27 and Jmjdla.

Disorders or conditions that can be prevented or treated by compounds and methods described herein include the prevention or treatment of cancer, such as cutaneous T-cell leukemia, head and neck tumors, pancreatic cancer, bladder cancer, high grade gliomas, brain metastasis, melanoma, skin cancer, lung cancer, breast cancer, prostate cancer, colon cancer, leukemia, myelodysplastic syndrome (a pre-leukemia condition), and multiple myeloma. In general, metastasis of any cancer can be prevented or treated with the compounds and methods described herein. The compounds can also be used to prevent or treat proliferative angiogenic conditions including telangectasia, venous angiomas, hemangioblastoma.

These compounds and methods can also be used to prevent or treat proliferative diseases or disorders of the skin, including topical dermatitis, psoriasis, and rosacea.

Furthermore, the compounds and methods that are described herein can be used to prevent or treat Central Nervous System ("CNS") diseases and conditions such as CNS inflammatory and conditions, e.g., multiple sclerosis and progressive multifocal leukoencephalopathy.

Moreover, the compounds and methods that are described herein can be used to prevent or treat inflammatory diseases and conditions, such as osteoarthritis, Rheumatoid arthritis, Crohn's disease, ulcerative colitis, and auto-immune diseases such as lupus and mixed auto-immune disease.

Diseases and conditions such as telangectasia, venous angiomas, hemangioblastoma, and polycythemia vera may also be advantageously prevented or treated with the compounds and methods described herein.

These compounds and methods can affect stem cell survival and differentiation by maintaining stem cell sternness, e.g., preventing the differentiation of stem cells.

The compounds taught herein may also be used for the augmentation of immune response, particularly where the augmentation of the immune response leads to the expression of costimulatory molecules on the peripheral macrophages and tumor-infiltrating microglia. These compounds are also useful when the immune response leads to proliferation of effector cells and/or up-regulation of several key intracellular signaling molecules that critically regulate T-cell and monocyte activation. The compounds are useful when the immune responses leads to up-regulation of several key intracellular signaling molecules that critically regulate T-cell and monocyte activation, particularly phosphorylation Syk (Tyr(152)) monocytes and ZAP-70 (Tyr(319)) in T cells.

Table 1 as found immediately below describes certain of the diseases and conditions that may be treated using the compounds described herein:

TABLE 1

Activation of STATs in Human Cancers

| Tumor Type | Activated STAT |
|---|---|
| Blood Tumors | |
| Multiple myeloma | STAT1, STAT3 |
| Leukaemias: | |
| HTLV-1-dependent | STAT3, STAT5 |
| Erythroleukaemia | STAT1, STAT5 |
| Acute myelogenous leukaemia (AML) | STAT1, STAT3, STAT5 |
| Chronic myelogenous leukaemia (CML) | STAT5 |
| Large granular lymphocyte leukaemia (LGL) | STAT3 |
| Lymphomas: | |
| EBV-related/Burkitt's | STAT3 |
| Mycosis fungoides | STAT3 |
| Cutaneous T-cell lymphoma | STAT3 |
| Non-Hodgkins lymphoma (NHL) | STAT3 |
| Anaplastic large-cell lymphoma (ALCL) | STAT3 |
| Solid Tumors | |
| Breast Cancer | STAT1, STAT3, STAT5 |
| Head and neck cancer | STAT1, STAT3, STAT5 |
| Melanoma | STAT3 |
| Ovarian cancer | STAT3 |
| Lung cancer | STAT3 |
| Pancreatic cancer | STAT3 |
| Prostate cancer | STAT3 |
| Glioma | STAT3, STAT5 |

Based on references cited in REFS 12, 17, EBV, Epstein-Ban virus; HTLV-1, human T-lymphotrophic virus-1.

The STAT ("signal transducer and activator of transcription") protein family includes transcription factors which are specifically activated to regulate gene transcription when cells encounter cytokines and growth factors. In mammals, there are seven known members of the STAT family of proteins: STAT1, STAT2, STAT3, STAT4, STAT5a, STAT5b, and STAT6. Yu, H., Jove, R., *The STATS of Cancer—New Molecular Targets Come of Age*, Nature Reviews, 4:97-105 (2004). These seven proteins range in size from 750 and 850 amino acids. The STAT5a and STAT5b proteins, collectively referred to herein as "STAT5," are closely related but encoded by different genes, Yu, H., Jove, R., *The STATS of Cancer—New Molecular Targets Come of Age*, Nature Reviews, 4:97-105 (2004).

STAT proteins act as signal transducers in the cytoplasm and transcription activators in the nucleus. Kisseleva T. Bhattacharya S., Braunstein J., Schindler C. W., *Signaling Through the JAK/STAT Pathway, Recent Advances and Future Challenges*, Gene 285: 1-24 (2002). For example, STAT proteins transduce signals from cytokine receptors, growth factor receptors, and non-receptor, cytoplasmic tyrosine kinases such as Src and Abl to the nucleus of a cell, where they bind DNA and regulate transcription of an assortment of genes. Id. As a result, STAT proteins regulate physiological functions such as immune response, inflammation, proliferation, differentiation, survival, metastasis, apoptosis, and immuno tolerance (e.g. tumor immune evasion). Xie, T. et al., *Stat3 Activation Regulates the Expression of Matrix Metalloprateinase-2 and Tumor Invasion and Metastasis*, Oncogene 23: 3550-3560 (2004); Levy, D. E., Inghirami, G., *STAT3: A Multifaceted Oncogene*, PNAS 103: 10151-52 (2006).

STATs share structurally and functionally conserved domains including: an N-terminal domain that strengthens interactions between STAT dimers on adjacent DNA-binding sites; a coiled-coil STAT domain that is implicated in protein-protein interactions; a DNA-binding domain with an immunoglobulin-like fold similar to p53 tumor suppressor protein; an EF-hand-like linker domain connecting the DNA-binding and SH2 domains; an SH2 domain that acts as a phosphorylation-dependent switch to control receptor recognition and DNA-binding; and a C-terminal transactivation domain. Chen X., Vinkemeier U., Zhao Y., Jentzalmi D., Darnell J. E., Kuriyan J., *Crystal Structure of a Tyrosine Phosphorylated STAT-1 Dimer Bound to DNA*, Cell 93: 827-839 (1998). In order to bind DNA, STAT proteins must dimerize. Yu, H., Jove, R., *The STATS of Cancer—New Molecular Targets Come of Age*, Nature Reviews, 4:97-105 (2004), Darnell, J. Jr., *Validating Stat3 in Cancer Therapy*, Nature Medicine, 11:595-96 (2005). Dimer formation involves reciprocal interaction between a SRC-homology 2 (SH2) domain of one STAT molecule with a phosphotyrosine residue of a second STAT molecule.

STAT proteins have been found to be overactive and/or persistently activate in cancer cells, including solid tumors and blood, malignancies, proliferative diseases of the skin, and inflammatory diseases. Yu, ft, Jove, R., *The STATS of Cancer—New Molecular Targets Come of Age*, Nature Reviews, 4:97-105 (2004). For example, STAT signaling has been implicated in various cancers, Song, J. I. and Grandis, J. R., *STAT Signaling in Head and Neck Cancer*, Oncogene, 19: 2489-2495, 2000; Nikitakis, N. G. et al., *Targeting the STAT Pathway in Head and Neck Cancer: Recent Advances and Future Prospects*, Current Cancer Drug Targets, 4:639-651. An increased presence of activated STAT3 and/or STAT5 in the nucleus is associated with dysregulation of gene transcription Yu, H., Jove, R., *The STATS of Cancer—New Molecular Targets Come of Age*, Nature Reviews, 4:97-105. Further, an increased presence of STAT3 and/or STAT5 is associated with increased transcription of genes which contribute to a cell proliferation, survival, angiogenesis, and tumor-induced immunotolerance. Yu, H, Jove, R., *The STATS of Cancer—New Molecular Targets Come of Age*, Nature Reviews, 4:97-105. For example, STAT5 is activated, in certain leukemias, breast cancer, and head and neck cancer. Yu, H., Jove, R., *The STATS of Cancer—New Molecular Targets Cone of Age*, Nature Reviews, 4:97-105. Similarly, STAT3 activation is known to abrogate growth factor dependence which contributes to certain carcinoma tumor growth. Kijima, T., Niwa, H., Steinman, R. A., Drenning, S. D., Gooding, W. E., Wentzel, A. L., Xi, S., and Grandis, J. R., *STAT3 Activation Abrogates Growth Factor Dependence And Contributes To Head And Neck Squamous Cell Carcinoma Tumor Growth In Vivo*, Cell Growth Differ, 13: 355-362, 2002, Activation of STAT3 is also reported to regulate survival in human non-small cell carcinoma cells. Song, L., Turkson. J., Karras, J. G, Jove, R., and Haura, E. B., *Activation Of Stat3 By Receptor Tyrosine Kinases And Cytokines Regulates Survival In Human Non-Small Cell Carcinoma Cells*, Oncogene, 22: 4150-4165, 2003. Accordingly, STAT3 and STAT5 are useful targets in treating STAT3- and STAT5-mediated disease.

Both STAT3- and STAT5-signaling pathways involve binding of cytokines or growth factors to cell-surface receptors, which leads to activation of cytoplasmic tyrosine kinases, such as the JAK family, which subsequently leads to phosphorylation of STAT monomers. Gadina, M., Hilton, D., Johnston, J. A., Morinobu, A., Lighvani, A., Zhou, Y. J., Visconti, R., O'Shea, J. J. *Signaling by Type I and Type H Cytokine Receptors: Ten Years After*, Curr. Opin. Immunol. 2001, 13: 363. STAT proteins are activated by phosphorylation causing them to dimerize and translocate to the nucleus, where they bind to specific promoter sequences in target genes. Horvath, C. M., *The Jak-STAT Pathway Stimulated by Interferon Gamma*, Science, STKE, 2004, 260: tr8.

Figure 5:
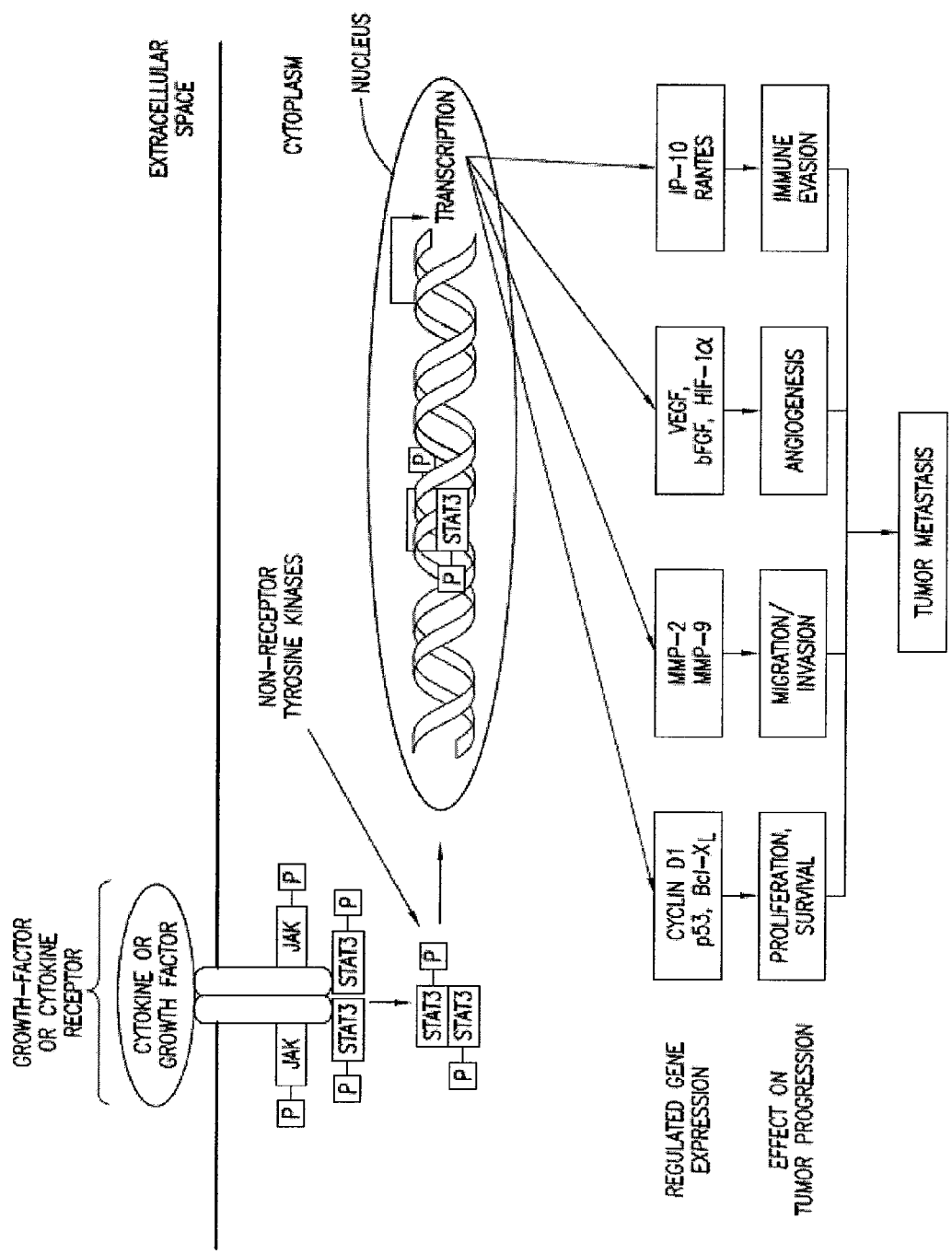
FIG. 5 is a schematic representation of signaling pathways which lead to STAT activation and STAT-mediated gene expression.

As shown schematically in FIG. 5, growth factor receptors, cytokine receptors and non-receptor tyrosine kinases have signaling pathways that converge on STAT3 and STAT5. For STAT3, these receptors and kinases include IL-2, IL-6, IL-7, IL-9, IL-10, IL-11, IL-15, IL-21, EGF, OSM, G-CSF, TPO, LIF and GH. For STAT5, the receptors and kinases include IL-2, IL-3, IL-7, IL-9, IL-15, G-CSF, GM-CSF, EPO, TPO, GH, and PRL.

More specifically, STAT3 activation is known to be mediated by EGFR, EPO-R, and IL-6 R via c-Src or JAK2. See e.g., Lai, S. Y., Childs, E. E., Xi, S., Coppelli, F. M., Gooding, W. E., Wells, A., Ferris, R. L., and Grandis, J. R., *Erythropoietin-Mediated Activation of JAK-STAT Signaling Contributes to Cellular Invasion in Head and Neck Squamous Carcinoma*, Oncogene, 24: 4442-4449, 2005; Siavash, H., Nikitakis, N. G., and Sauk, *Abrogation of IL-6-Mediated JAK Signalling by the Cyclopentenone Prostaglandin 15d-PGJ(2) in Oral Squamous Carcinoma Cells*, Br J Cancer, 91: 1074-1080, 2004; & Quadros, M. R., Peruzzi, F., Kari, C., and Rodeck, U., *Complex Regulation of Signal Transducers and Activators of Transcription 3 Activation in Normal and Malignant Keratinocytes*, Cancer Res, 64: 3934-3939, 2004. MAPK activation can lead to decreased STAT3 phosphorylation. In solid tumors, PDGFR and c-Met can also activate STAT3 via c-Src. IGFR1 and EGFR can activate STAT3 in a JAK-Independent manner. STAT3 activation can lead to activation of several downstream target genes including Bcl-XL, cyclin D1 and VEGF.

Ligand binding to a cell-surface cytokine receptor triggers activation of JAKs. With increased kinase activity, JAK phosphorylates tyrosine residues on the receptor and creates sites for interaction with proteins that contain phosphotyrosine-binding SH2 domain. STATs possessing SEE domains capable of binding these phosphotyrosine residues are recruited to the receptors and are tyrosine-phosphorylated by JAKs. The phosphotyrosine then acts as a docking site for SH2 domains of other STATs, mediating their dimerization, Different STATs form hetero- as well as homodimers. Activated STAT dimers accumulate in the cell nucleus and activate transcription of their target genes. Hebenstreit D. et al. (2005) Drug News Perspect. Vol. 18 (4), pages 243-249. STATs can be tyrosine-phosphorylated by other non-receptor tyrosine kinases, such as c-src, as well as receptor tyrosine kinases, such as the epidermal growth factor receptor.

Likewise, the binding of IL-6 family cytokines (including IL-6, oncostatin M and leukemia inhibitory factor) to the gp130 receptor triggers STAT3 phosphorylation by JAK2. Boulton, T G, Zhong, Z, Wen, Z, Darnell, Jr, J E, Stahl, N, and Yancopoulos. G D, *STAT3 Activation by Cytokines Utilizing gp130 and Related Transducers Involves is Secondary Modification Requiring an H7-Sensitive Kinase* Proc Natl Acad Sci USA. 92(15): 6915-6919. EGF-R and certain other receptor tyrosine kinases, such as c-MET phosphorylate STAT3 in response to their ligands. Yuan Z L et al.; (2004) Mol. Cell. Biol. Vol. 24 (21), pages 9390-9400. STAT3 is also a target of the c-src non-receptor tyrosine kinase. Silva C. M. (2004) Oncogene Vol. 23 (48), pages 8017-8023. In addition to STAT3 activation through IL-6 binding, STAT3 is further activated by binding of IL-2. IL-7, IL-9, IL-10, IL-21, EGF, OSM, G-CSF, TPO, LIE, or GH to an appropriate receptor. Similarly; STAT5 is activated by binding of IL-2; IL-3, IL-5, IL-7, G-CSF, GM-CST, EPO, TPO, GH, or PRL to an appropriate receptor.

Indeed, Janus kinases ("JAK") play an important role in the initial steps of cytokine receptor signaling. While the specificity of the four members of the JAK family (Jak1, Jak2, Jak3, and Tyk2) for different cytokine receptors is not fully understood, studies report that certain specific cytokine receptors can activate one or more Jak. O'shea, J. J., Peso, M. Boric, D. C., Changelian, P. S., *A New Modality for Immunosuppression: Targeting the JAK/STAT Pathway*, Nature Rev. Drug Disc. 2004 (3): 555-564. For example, the growth hormone receptor (GHR) may interact predominantly with Jak2, and has been shown that to induce phosphorylation of Jak1 and Jak3. Hellgren, G., Jansson, J. O., Carlsson, L. M., Carlsson, B. *The Growth Hormone Receptor Associates with Jak1, Jak2 and Tyk2 in Human Liver*, Growth Horm. IGF Res. 1999 9(3):212-8.

The JAK-STAT pathway can be negatively regulated on multiple levels. Protein tyrosine phosphatases remove phosphates from cytokine receptors as well as activated STATs Hebenstreit D. et al. (2005) Drug News Perspect. Vol. 18 (4), pages 243-249. More recently, identified Suppressors of Cytokine Signaling (SOCS) inhibit STAT phosphorylation by binding and inhibiting JAKs or competing with STATs for phosphotyrosine binding sites on cytokine receptors, Krebs, L. et al. (2001) Stem Cells Vol. 19, pages 378-387. STATs are also negatively regulated by Protein Inhibitors of Activated STATs (PIAS), which act in the nucleus through several mechanisms. Shuai., K. (2006) Vol. 16 (2), pages 196-202. For example, PIAS1 and PIAS3 inhibit transcriptional activation by STAT1 and STAT3 respectively by binding and blocking access to the DNA sequences they recognize.

The JAK-STAT signaling pathway takes part in the regulation of cellular responses to cytokines and growth factors, Employing Janus kinases (JAKs) and Signal Transducers and Activators of Transcription (STATs), the pathway transduces the signal carried by these extracellular polypeptides to the cell nucleus, where activated STAT proteins modify gene expression. Although STATs were originally discovered as targets of Janus kinases, certain stimuli can activate them independent of JAKs. D W Leaman, S Pisharody, T W Flickinger, M A Commane, J Schlessinger, I M Kerr, D E. Levy, and G R Stark *Roles of JAKs in Activation of STATs and Stimulation of c-fos Gene Expression by Epidermal Growth Factor*, Mol Cell Biol. 1996 16(1): 369-375. This pathway plays a central role in principal cell fate decisions, regulating the processes of cell proliferation, differentiation and apoptosis. STAT activator phosphorylation requires phosphorylation of JAK to phosphorylate. In other words, JAK must first phosphorylate and bind to STAT. STAT is then able to phosphorylate and dimerize with another STAT.

The compounds described herein can control cell growth and survival via STAT modulation. Cell activity is regulated by "signals." Signals enter cell walls through receptors, Signals are transduced by STATs. STATs complete a pathway to DNA. Signals activate DNA transcription (otherwise referred to as gene activation). BCL-Xl, MCL1, Surivin and p53 are involved in cell survival. MYC, Cyclin D1/D2 and p53 are involved in cell proliferation. Downstream of the phosphorylation of STAT3, signaling pathways cause angiogenesis as a result of regulation of VEGF, HIF1 and p53, and immune evasion as regulated by immune-suppressing factors, pro-inflammatory cytokines and pro-inflammatory chemokines.

The compounds and methods described herein can directly or indirectly modulate STAT3 and/or STAT5 activation. For example, the compounds and methods can inhibit STAT3 activation by: (1) affecting signaling pathways which lead to STAT3 or STAT5 activation, such that the downstream activation of STAT3 or STAT5 is prevented or reduced; (2) directly preventing or reducing STAT3 or STAT5 activation, e.g., by preventing phosphorylation of STAT3 or STAT5; and (3) disrupting complexation of STAT3 or STAT5 with any number of cofactors and/or macromolecules, where the complexes are responsible for regulation of STAT3 or STAT5 signaling, and likewise STAT5 activation.

Inhibition of STAT3 and/or STAT5 activation can be accomplished, directly or indirectly, through any of the STAT targeting strategies currently known in the art. By way of example only, STAT3 activity might be decreased by: (1) reducing the availability of STAT3 or STAT5 molecules for recruitment; (2) blocking STAT3 or STAT5 recruitment to receptors, (3) blocking phosphorylation of STAT3 or STAT5 molecules; (4) interfering with the formation of STAT3 or STAT5 dimers; (5) interference with translocation of STAT3 or STAT5 dimers into the nucleus; (6) interference of STAT3 or STAT5 binding to DNA; (7) interference of STAT3 or STAT5 interaction with transcriptional activators; and/or (8) other methods of preventing STAT-mediated transcriptional activation. See e.g., N. G. Nikitakis, et al., *Targeting the STAT Pathway in Head and Neck Cancer: Recent Advances and Future Prospects*, Current Cancer Drug Targets, 4: 637-651 (2004).

Direct or indirect modulation of STAT3 or STAT5 activity by the compounds presented herein can prevent, reduce, or eliminate STAT3- and/or STAT5-dependent activation of genes responsible for proliferation, survival, metastasis, angiogenesis, immune response, and tumor immune evasion. As shown schematically, in FIGS. 5 and 6, STAT3 and/or STAT5 activation have an effect on the transcription of many genes including, but not limited to VEGF, MMP9, MMP2, survivin, c-Myc, MMP-1, MEK-5, c-FOS, COX-2, Bcl-xL, MMP-10, HSP27, Jmjdla, PGE-2.

These activated STAT effects on the transcription of certain genes are likewise associated with physiological effects. For example, as reported by Yu and Jove at pages 99-101, which are incorporated by reference herein, activated STATs promote cell survival by up-regulating Bcl-xL, MCL1, and surviving, and down-regulating p53. Yu, H., et al., *The STATS of Cancer—New Molecular Targets Come of Age*, Nature Reviews, 4:97-105 (2004). Activated. STATs also support proliferation by up-regulating MYC and cyclin D1/D2 and down-regulating p53. Additionally, activated STATs support angiogenesis through up-regulation of VEGF and HIF1., and down regulation of p53. Furthermore, activated STATs also aid tumor immune evasion by up-regulating immune-suppressing factors and down-regulating pro-inflammatory cytokines and chemokines.

Besides being useful for human treatment, the compounds and formulations of the present invention are also useful for veterinary treatment of companion animals, exotic animals and farm animals, including mammals, rodents, and the like. More preferred animals include horses, dogs, and cats.

General Synthetic Methods for Preparing Compounds

The following schemes can be used to practice the present invention.

Synthesis and Characterization

Synthesis of
(E)-3-(6-bromopyridin-2-yl)acrylaldehyde

Solution of 6-bromo-2-carboxypyridine (3 g, 16.1 mmol) was dissolved in dichloromethane (100 mL). (Triphenylphosphoranylidene)acetaldehyde (4.9 g, 16.1 mmol) was added and obtained mixture was stirred at room temperature for 5 hrs. Dichloromethane was partially evaporated (to the volume about 50 mL) and reaction mixture was applied on chromatography column (SilicaGel 60) Products were eluted with dichloromethane. Fractions containing product were combined and evaporated to give 2.3 g of white powder (Yield 67%).

$^1$HNMR (CDCl3, δ) ppm: 9.81 (4, 1H, J=7.6 Hz, CHO), 7.63 (dd, 1H, J=J=7.7 Hz, H4), 7.51 (dd, 2H, J=J=7.7 Hz, H-3.5), 7.45 (d, 1H, J=15.8 Hz, Ar—CH═CH—CHO), 7.12 (dd, 1H, 1H, J=15.8 Hz, J=7.6 Hz, Ar—CH═CH—CHO)

General Procedure: Synthesis of (2E,4E)-5-(6-bromopyridin-2-yl)-2-cyano-N-substituted-2,4-dienamides Solution of (1) (2.1 g, 99 mmol) and piperidine (0.2 mL) in anhydrous ethanol was prepared. Aldehyde (10.6 mmol) was added and reaction mixture was stirred at room temperature. After 3 hrs obtained solid was filtered, washed with ethanol and dried. The compounds as illustrated in the following examples were made.

Example 1

(2E,4E)-5-(6-bromopyridin-2-yl)-2-cyano-N-[(1S)-1-phenylethyl]penta-2,4-dienamide

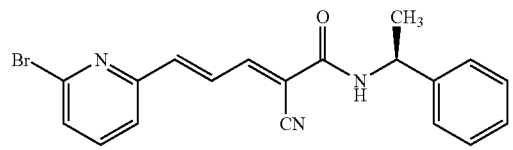 [SMILES: C[C@H](NC(=O)/C(C#N)=C/C=C/c1cccc(Cl)n1)c1ccccc1]

Yield 67% (2E,4E)-5-(6-bromopyridin-2-yl)-2-cyano-N—((S)-1-phenylethyl)penta-2,4-dienamide $^1$HNMR (CDCl3, δ) ppm: 8.07 (d, 1H, J=12.1 Hz, H-3), 7.71 (dd, 1H, J=12.1 Hz, J=15.0 Hz, H-4), 7.59 (dd, 1H, J=7.7 Hz, H-4'), 7.47 (d, 1H, J=7.5 Hz, H-3'), 7.41 (d, 1H, J=7.63 Hz, H-5'), 7.39-729 (m, 5H, H aromat), 7.15 (d, 1H, J=15.0 Hz, H-5), 6.45 (d, 1H, J=7.5 Hz, NH), 5.23 (dt, H, J=7.0 Hz, J=7.5 Hz, H-1"), 1.61 (d, 1H, J=7.0 Hz, Me).

Example 2

(2E,4E)-5-(6-chloropyridin-2-yl)-2-cyano-N-[(1S)-1-phenylethyl]penta-2,4-dienamide

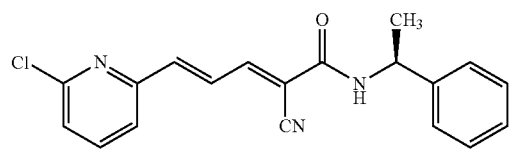

$^1$HNMR (CDCl3, δ) ppm: 8.07 (d, 1H, J=12.1 Hz, H-3), 7.73 (dd, 1H, J=12.0 Hz, J=15.0 Hz, H-4), 7.70 (dd, 1H, J=7.81 Hz, H-4'), 7.43-7.29 (m, 7H, H-3', H-5', H aromat), 7.18 (d, 1H, J=15.0 Hz, H-5), 6.45 (d, 1H, J=7.3 Hz, NH), 5.25 (dt, 1H, 7.0 Hz, J=7.5 Hz, H-1''), 1.61 (d, 1H, J=7.0 Hz, Me).

Example 3

(2E,4E)-5-(6-chloropyridin-2-yl)-2-cyano-N-[(1R)-1-phenylethyl]penta-2,4-dienamide

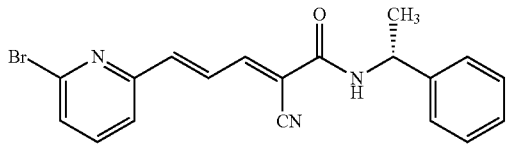 [SMILES: C[C@@H](NC(=O)/C(C#N)=C/C=C/c1cccc(Cl)n1)c1ccccc1]

¹HNMR (CDCl3, δ) ppm: 8.07 (d, 1H, J=12.1 Hz, H-3), 7.71 (dd, 1H, J=12.1 Hz, J=15.0 Hz, H-4), 7.59 (dd, 1H, J=J=7.7 Hz, H-4'), 7.47 (d, 1H, J=7.5 Hz, H-3'), 7.41 (d, 1H, J=7.63 Hz, H-5'), 7.39-7.29 (m, 5H, H aromat), 7.15 (d, 1H, J=15.0 Hz, H-5), 6.45 (d, 1H, J=7.5 Hz, NH), 5.23 (dt, 1H, J=7.0 Hz, J=7.5 Hz, H-1''), 1.61 (d, 1H, J=7.0 Hz, Me).

Example 4

(2E,4E)-N-benzyl-5-(6-bromopyridin-2-yl)-2-cyano-penta-2,4-dienamide

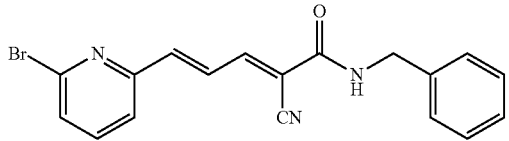

¹HNMR (CDCl3, δ) ppm: 8.10 (d, 1H, J=12.1 Hz, H-3), 7.70 (dd, 1H, J=12.1 Hz, J=15.0 Hz, H-4), 7.57 (d, 1H, J=7.7 Hz, H-4'), 7.46-7.29 (m, 7H, H-3', H-5', H aromat), 7.16 (d, 1H, J=15.0 Hz, H-5), 6.52 (bs, 1H, NH), 4.58 (d, 1H, J=5.8 Hz, 1'').

Example 5

(2E,4E)-5-(6-chloropyridin-2-yl)-2-cyano-N-[(1R)-1-phenylethyl]penta-2,4-dienamide

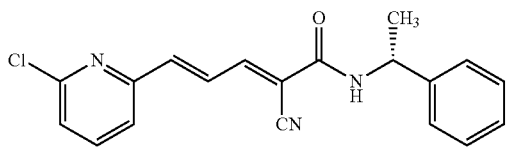

¹HNMR (CDCl3, δ) ppm: 8.07 (d, 1H, J=12.1 Hz, H-3), 7.73 (dd, 1H, J=12.0 Hz, J=15.0 Hz, H-4), 7.70 (dd, 1H, J=J=7.81 Hz, H-4'), 7.43-7.29 (m, 7H, H-3', H-5', H aromat), 7.18 (d, 1H, J=15.0 Hz, H-5), 6.45 (d, 1H, J=7.3 Hz, NH), 5.25 (dt, 1H, J=7.0 Hz, J=7.5 Hz, H-1''), 1.61 (d, 1H, J=7.0 Hz, Me).

Example 6

(2E,4E)-N-benzyl-5-(6-chloropyridin-2-yl)-2-cyano-penta-2,4-dienamide

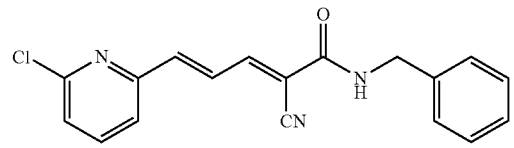 [SMILES: N#C/C(=C\C=C\c1cccc(Cl)n1)C(=O)NCc1ccccc1]

¹HNMR (CDCl3, δ) ppm: 8.09 (d, 1H, J=12.1 Hz, H-3), 7.72 (dd, 1H, J=12.1 Hz, J=15.0 Hz, H-4), 7.68 (dd, 1H, J==7.8 Hz, H-4'), 7.40-7.28 (m, 7H, H-3', H-5', H aromat), 7.17 (d, 1H, J=15.0 Hz, H-5), 6.45 (bs, 1H, NH), 4.58 (d, 1H, J=5.75 Hz, H-1'').

Example 7

(2E,4E)-5-(6-bromopyridin-2-yl)-2-cyano-N-[(S)-cyclopropyl(phenyl)methyl]penta-2,4-dienamide

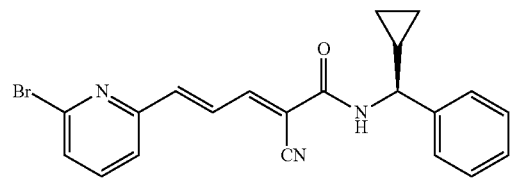 [SMILES: N#C/C(=C\C=C\c1cccc(Br)n1)C(=O)N[C@H](c1ccccc1)C1CC1]

¹HNMR (CDCl3, δ) ppm: 8.06 (d, 1H, 12.1 Hz, H-3), 7.72 (dd, 1H, J=12.1 Hz, J=15.0 Hz, H-4), 7.59 (dd, 1H, J=J=7.9 Hz, H-4'), 7.47-7.29 (m, 7H, H-3', H-5', H aromat), 7.15 (d, 1H, J=15.0 Hz, H-5), 6.68 (d, 1H, J=7.8 Hz, NH), 4.49 (dd, 1H, J=8.0 Hz, J=8.8 Hz, H-1''), 1.33-1.24 (m, 1H, H-2''), 0.69-0.41 (m, 4H, 3''-CH$_2$, 4''-CH$_2$).

Example 8

(2E,4E)-5-(6-bromopyridin-2-yl)-2-cyano-N-[(1S)-1-phenylpropyl]penta-2,4-dienamide

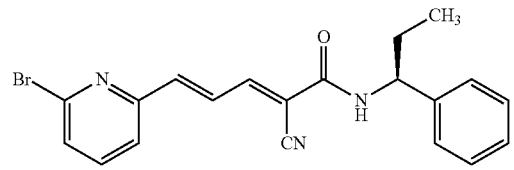 [SMILES: CC[C@H](NC(=O)/C(C#N)=C/C=C/c1cccc(Br)n1)c1ccccc1]

¹HNMR (CDCl3, δ) ppm: 8.03 (dd, J=12.1 Hz, J=0.7 Hz, 7.69 (dd, 1H, J=12.1 Hz, J=15.0 Hz, H-4), 7.57 (dd, 1.171, J=7.5 Hz, J=7.9 Hz, H-4'), 7.45 (dd, J=7.9 Hz, J=0.8 Hz, H-3), 7.39 (dd, 1H, J=7.5 Hz, J=0.8 Hz, H-5), 7.39-7.27 (m, 5H, H aromat), 7.1 (d, 1H, J=15.0 Hz, H-5), 6.43 (d, 1H, J=7.8 Hz, NH), 4.96 (dd, J=15.2 Hz, J=7.5 Hz, H-1"), 1.99-1.85 (m, 2H, H-2"), 0.93 (t, 3H, J=7.4 Hz, H-3").

Example 9

(2E,4E)-5-(6-bromopyridin-2-yl)-2-cyano-N-[(1S)-1-phenylbutyl]penta-2,4-dienamide

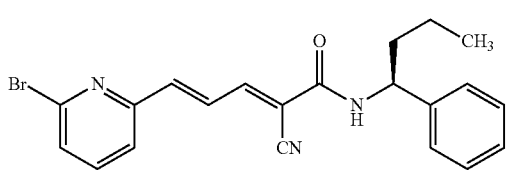 [SMILES: CCC[C@H](NC(=O)/C(C#N)=C/C=C/c1cccc(Br)n1)c1ccccc1]

¹HNMR (CDCl3, δ) ppm: 8.03 (dd, 1H, J=12.1 Hz, J=0.7 Hz, H-3), 7.68 (dd, 1H, J=15.0 Hz, J=12.1 Hz, H-4), 7.55 (dd, 1H, J=J=7.7 Hz, H-4'), 7.45 (dd, 1H, J=7.9 Hz, J=0.8 Hz, H-3'), 7.39 (dd, 1H, J=7.5 Hz, J=0.8 Hz, H)-5'), 6.66-7.28 (m, 6H, H-4, H-arom), 7.13 (d, 1H, J=14.9 Hz, H-5), 6.42 (d, 1H, J=8.0 Hz, NH), 5.05 (dd, 1H, J=15.3, J=7.6 Hz, H-1"), 1.91-1.82 (m, 2H-2"), 1.41-1.24 (m, 2H, H-3"), 0.95 (t, 3H, J=7.3 Hz, H-4").

The antiproliferative activity of the Compound of Example 1 and Example 7 have been shown in a Colo357FG pancreatic cancer cell line as follows:

| Compound | Colo357FG IC50 μM |
|---|---|
| Example 1 | 3.2 |
| Example 7 | 5.4 |

The activity of the compounds as STAT inhibitors in Examples 1, 2, 4, and 9 has been shown by at least one of the following assays. The associated activity data obtained is provided in FIGS. 1 through 4. The other compounds described above, which have not yet been made, are predicted to have activity in these assays as well.

Biological Activity Assay

MTT Method for Determining Cell Viability and Drug Dose-Response

A variety of cell types were seeded at a density of 50,000 cells/100 μl per well Onto 96-well plates and cultured for 24-48 h DMEM medium until they reached confluency. At confluency, 25 μl of fresh media containing WP1220 at various concentrations (0 to 100 μM) was added to the wells and incubated for 72 h at 37° C. The complex was removed, 100 of fresh medium was added and the cells were incubated overnight. Medium was removed and fresh medium (100 μl) was added to each well along with (20 μl) MTT solution (5 mg/ml in PBS) before incubating the cells for a further 4 h at 37° C. The reaction product was solubilised with sodium dodecyl sulfate (100 μl, 10%, w/v) in 0.01 N HCl overnight before quantifying the product using a microplate reader at 590 nm and comparing with control cells. The experiment was carried out in triplicate (n=3).

Biological Activity Assay

Western Blot Methods for Determining Protein and Phosphoprotein Content

Using phospho-tyrosine STAT3 (Y705), phospho-tyrosine Jak2 (Y1007/1008), total STAT3, total Jak2, Bcl-xL, actin (Cell Signaling Technology, Danvers, Mass.), and survivin (R&D Systems, Minneapolis, Minn.) antibodies, western blots were performed using the following methods. Briefly, (1) Samples were prepared from cells that were homogenized in a buffer protecting the protein of interest from degradation; (2) The sample was then separated using SDS-PAGE (10-15 μg protein/well) and then transferred to a membrane for detection; and (3) The membrane was incubated with a generic protein (milk proteins) to bind to any remaining sites on the membrane. A primary antibody was then added to the solution which is able to hind to its specific protein; (4) A secondary antibody-enzyme conjugate, which recognizes the primary antibody was then added to find locations where the primary antibody has bound.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of structural Formula I:

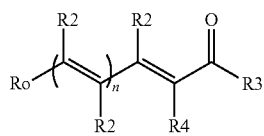

or a pharmaceutically acceptable salt thereof, wherein:
n is an integer selected from 1, 2, or 3;
$R_0$ is $R_1$ or $R_1$—$Z_1$—;
$Z_1$ is alkyl;
$R_1$ is:

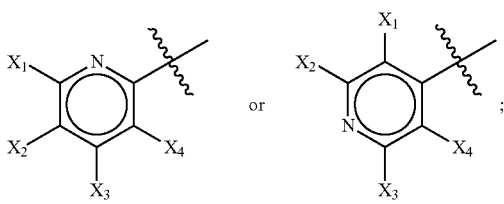

$X_1$, $X_2$, $X_3$, and $X_4$ are each independently hydrogen, halogen, alkyl, alkoxy, OH, trihalomethyl, or $NO_2$;
$R_2$ is alkyl, alkenyl, alkynyl, alkoxy, alkylaryl, halogen, hydrogen, OH, $NO_2$, thioether, amine, or SH;
$R_3$ is:

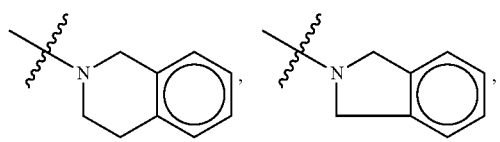

-continued

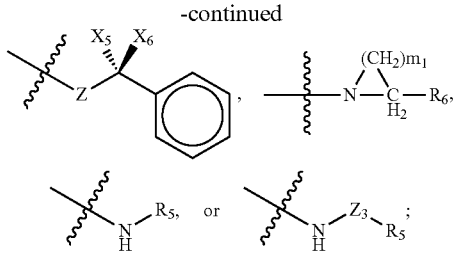

$m_1$ is an integer selected from 1, 2, 3, or 4;

$X_5$ and $X_6$ are each independently hydrogen, alkyl, aryl, alkoxyl, aryloxy, cycloalkyl, aralkyl, alkylester, alkylesteralkyl, alkylacetoxyl, hydroxyl, or hydroxylalkyl;

Z is NH, S, or O;

$Z_3$ is alkyl;

$R_4$ is CN, substituted amine, $CH_2S$-alkyl, alkyl, or $CH_2N_3$;

$R_5$ and $R_6$ are each independently selected from the group consisting of:

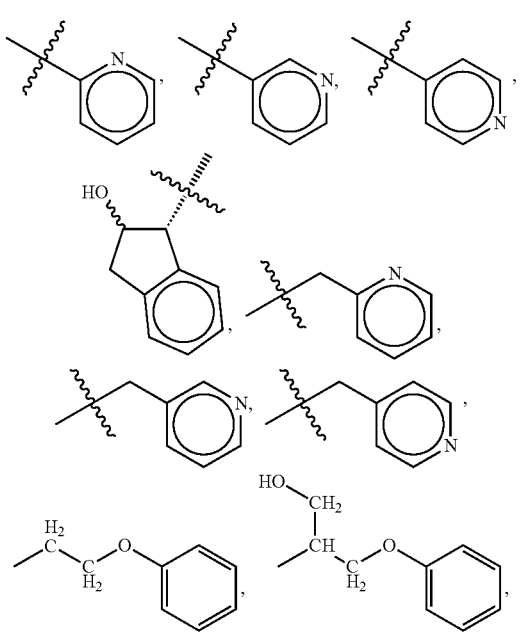

monosaccharide, polysaccharide, acetylated monosaccharide 1,2,3,4-diisopropylideno-D-galactose, substituted aryl, unsubstituted aryl, and unsubstituted alkylaryl; and at least one of $X_5$ and $X_6$ is selected from the group consisting of alkyl, cycloalkyl, aralkyl, alkylester, alkylesteralkyl, alkylacetoxyl, and hydroxylalkyl, or at least one of $X_1$, $X_2$, $X_3$, and $X_4$ is halogen.

2. The compound as recited in claim 1, wherein:

n is 1;

$R_0$ is $R_1$;

$X_1$, $X_2$, $X_3$, and $X_4$ are each independently hydrogen, halogen, alkyl, alkoxy, OH, trihalomethyl, or $NO_2$;

$R_2$ is hydrogen;

$R_3$ is:

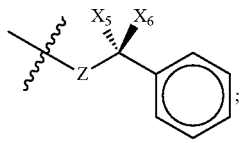

$X_5$ and $X_6$ are each independently hydrogen, alkyl, cycloalkyl, aralkyl, alkylester, alkylesteralkyl, alkylacetoxyl, or hydroxylalkyl;

Z is NH; and $R_4$ is CN.

3. The compound as recited in claim 2, wherein at least one of $X_5$ and $X_6$ is selected from the group consisting of alkyl, cycloalkyl, aralkyl, alkylester, alkylesteralkyl, alkylacetoxyl, and hydroxylalkyl.

4. The compound as recited in claim 3, wherein at least one of $X_1$, $X_2$, $X_3$, and $X_4$ is halogen.

5. The compound as recited in claim 3, wherein $R_1$ is:

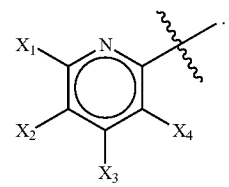

6. The compound as recited in claim 5, wherein:

$X_1$ is halogen;

$X_2$, $X_3$, and $X_4$ are each independently hydrogen, halogen, alkyl, alkoxy, OH, trihalomethyl, or $NO_2$; and $X_5$ and $X_6$ are each independently hydrogen, cyclopropyl, or $—CH_3$.

7. The compound as recited in claim 5, wherein:

$X_1$ is Br or Cl; and $X_2$, $X_3$, and $X_4$ are each hydrogen.

8. The compound as recited in claim 7, wherein:

$X_5$ and $X_6$ are each independently hydrogen, cyclopropyl, or $—CH_3$.

9. A pharmaceutical composition comprising a compound as recited in claim 1, together with a pharmaceutically acceptable carrier.

10. The pharmaceutical composition as recited in claim 9, wherein said pharmaceutical composition is a topical pharmaceutical composition.

11. A pharmaceutical composition comprising a compound as recited in claim 2, together with a pharmaceutically acceptable carrier.

12. The pharmaceutical composition comprising as recited in claim 11, wherein said pharmaceutical composition is a topical pharmaceutical composition.

13. A pharmaceutical composition comprising a compound as recited in claim 7, together with a pharmaceutically acceptable carrier.

14. The pharmaceutical composition as recited in claim 13, wherein said pharmaceutical composition is a topical pharmaceutical composition.

15. A pharmaceutical composition comprising a compound as recited in claim 8, together with a pharmaceutically acceptable carrier.

16. The pharmaceutical composition comprising as recited in claim 15, wherein said pharmaceutical composition is a topical pharmaceutical composition.

* * * * *

UNITED STATES PATENT AND TRADEMARK OFFICE
CERTIFICATE OF CORRECTION

PATENT NO. : 8,637,675 B2
APPLICATION NO. : 13/401161
DATED : January 28, 2014
INVENTOR(S) : Waldemar Priebe et al.

It is certified that error appears in the above-identified patent and that said Letters Patent is hereby corrected as shown below:

On the Title Page

In title page, item (56) References Cited - Other Publications, delete the 4th reference on page 1 "Alconet al., "Activation of Tyrosine Kinase Pathway by Vanadate in Gallbladder Smooth Muscle," *Biochem. Pharmacol.*, 59: 1077-1089, 2000." and replace with --Alcon et al., "Activation of Tyrosine Kinase Pathway by Vanadate in Gallbladder Smooth Muscle," *Biochem. Pharmacol.*, 59: 1077-1089, 2000.-- therefor.

In title page, item (56) References Cited - Other Publications, delete the 1st reference on page 2 "Arbelet al., "Inhibitors that target protein kinases for the treatment of ovarian carcinoma," *Am. J Obstet. Gynecol*, 188(5): 1283-90, 2003." and replace with --Arbel et al., "Inhibitors that target protein kinases for the treatment of ovarian carcinoma," *Am. J Obstet. Gynecol*, 188(5): 1283-90, 2003.-- therefor.

In title page, item (56) References Cited - Other Publications, delete the 2nd reference on page 2 "Bartholomeuszet al., "Degrasyn activates proteasomal-dependent degradation of c-Myc," *Cancer Research*, 67(8):3912-3918, 2007." and replace with --Bartholomeusz et al., "Degrasyn activates proteasomal-dependent degradation of c-Myc," *Cancer Research*, 67(8):3912-3918, 2007.-- therefor.

In title page, item (56) References Cited - Other Publications, delete the 3rd reference on page 2 "Bartonet al., "Signal transducer and activator of transcription 3 (STAT3) activation in prostate cancer: direct STAT3 inhibition induces apoptosis in prostate cancer lines," *Molecular Cancer Therapeutics*, 3(1): 11-20, 2004." and replace with --Barton et al., "Signal transducer and activator of transcription 3 (STAT3) activation in prostate cancer: direct STAT3 inhibition induces apoptosis in prostate cancer lines," *Molecular Cancer Therapeutics*, 3(1): 11-20, 2004.-- therefor.

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,637,675 B2

In title page, item (56) References Cited - Other Publications, delete the 4th reference on page 2 "Bhartiet al., "Curcumin (diferuloylmethane) inhibits constitutive and IL-6-inducible STAT3 phosphorylation in human multiple myeloma cells," *J. Immunol.*, 171(7):3863-3871, 2003." and replace with --Bharti et al., "Curcumin (diferuloylmethane) inhibits constitutive and IL-6-inducible STAT3 phosphorylation in human multiple myeloma cells," *J. Immunol.*, 171(7):3863-3871, 2003.-- therefor.

In title page, item (56) References Cited - Other Publications, delete the 5th reference on page 2 "Burdelyaet al., "Combination therapy with AG-490 and interleukin 12 achieves greater antitumor effects than either agent alone," *Mol. Cancer Ther.*, 1(11):893-9, 2002." and replace with --Burdelya et al., "Combination therapy with AG-490 and interleukin 12 achieves greater antitumor effects than either agent alone," *Mol. Cancer Ther.*, 1(11):893-9, 2002.-- therefor.

In title page, item (56) References Cited - Other Publications, delete the 6th reference on page 2 "Burkeet al., "Inhibition of constitutively active Stat3 suppresses growth of human ovarian and breast cancer cells," *Oncogene*, 20:7925-7934, 2001." and replace with --Burke et al., "Inhibition of constitutively active Stat3 suppresses growth of human ovarian and breast cancer cells," *Oncogene*, 20:7925-7934, 2001.-- therefor.

In title page, item (56) References Cited - Other Publications, delete the 25th reference on page 2 "CASRN 477972-73-9, STN Entry Date Jan. 2, 2003." and replace with --CAS RN 477972-73-9, STN Entry Date Jan. 2, 2003.-- therefor.

In title page, item (56) References Cited - Other Publications, delete the 26th reference on page 2 "Catlett-Falconeet al., "Constitutive activation of Stat3 signaling confers resistance to apoptosis in human U266 myeloma cells," *Immunity*, 10(1): 105-15, 1999." and replace with --Catlett-Falcone et al., "Constitutive activation of Stat3 signaling confers resistance to apoptosis in human U266 myeloma cells," *Immunity*, 10(1): 105-15, 1999.-- therefor.

In title page, item (56) References Cited - Other Publications, delete the 27th reference on page 2 "Chenet al., "Crystal structure of a tyrosine phosphorylated STAT-1 dimer bound to DNA," *Cell*, 93:827-839, 1998." and replace with --Chen et al., "Crystal structure of a tyrosine phosphorylated STAT-1 dimer bound to DNA," *Cell*, 93:827-839, 1998.-- therefor.

In title page, item (56) References Cited - Other Publications, delete the 28th reference on page 2 "Chenet al., "Human pancreatic adenocarcinoma: in vitro and in vivo morphology of a new tumor line established from ascites," *In Vitro*, 18(1):24-34, 1982." and replace with --Chen et al., "Human pancreatic adenocarcinoma: in vitro and in vivo morphology of a new tumor line established from ascites," *In Vitro*, 18(1):24-34, 1982.-- therefor.

In title page, item (56) References Cited - Other Publications, delete the 29th reference on page 2 "Constantinet al., "Tyrphostin AG490, a tyrosine kinase inhibitor, blocks actively induced experimental autoimmune encephalomyelitis," *Eur. J Immunol.*, 28(11):3523-9, 1998." and replace with --Constantin et al., "Tyrphostin AG490, a tyrosine kinase inhibitor, blocks actively induced experimental autoimmune encephalomyelitis," *Eur. J Immunol.*, 28(11):3523-9, 1998.-- therefor.

CERTIFICATE OF CORRECTION (continued)
U.S. Pat. No. 8,637,675 B2

In title page, item (56) References Cited - Other Publications, delete the 32nd reference on page 2 "De Voset al., "JAK2 tyrosine kinase inhibitor tyrphostin AG490 downregulates the mitogen-activated protein kinase (MAPK) and signal trasducer and activator of transcription (STAT) pathways and induces apoptosis in myeloma cells," *Br. J. Haematol.* 109:823-828, 2000." and replace with --De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells," *Br. J. Haematol.* 109:823-828, 2000.-- therefor.

In title page, item (56) References Cited - Other Publications, delete the 33rd reference on page 2 "Duqueet al., "Structure of N-benzyl-[Duqueet al., Structure of N-benzyl-[2-cyano-3-(2'-furyl)acrylamide], Revista CENIC," *Ciencias Quimicas*, 27(1-2-3):25-29, 1996." and replace with --Duque et al., "Structure of N-benzyl-[2-cyano-3-(2'-furyl)acrylamide], Revista CENIC," *Ciencias Quimicas*, 27(1-2-3):25-29, 1996.-- therefor.

In title page, item (56) References Cited - Other Publications, delete the 34th reference on page 2 "Durruthyet al., "Structure of N-(2-furylmethyl)-alpha-cyano-2-furanacrylamide," *Acta Crystallographica, Section C: Crystal Structure Communications*, C49(3):558-559, 1993." and replace with --Durruthy et al., "Structure of N-(2-furylmethyl)-alpha-cyano-2-furanacrylamide," *Acta Crystallographica, Section C: Crystal Structure Communications*, C49(3):558-559, 1993.-- therefor.

In title page, item (56) References Cited - Other Publications, delete the 35th reference on page 2 "Epling-Burnetteet al., "Inhibition of STAT3 signaling leads to apoptosis of leukemic large granular lymphocytes and decreased Mc1-1 expression," The Journal of Clinical Investigation, 107(3):351-362, 2001." and replace with --Burnette et al., "Inhibition of STAT3 signaling leads to apoptosis of leukemic large granular lymphocytes and decreased Mc1-1 expression," *The Journal of Clinical Investigation*, 107(3):351-362, 2001.-- therefor.

In title page, item (56) References Cited - Other Publications, delete the 38th reference on page 2 "Ferrajoliet al., "WP1066 disrupts janus kinase-2 and induces caspase-dependent apoptosis in acute myelogenous leukemia cells," *Cancer Research*, 67(23): 11291-11299, 2007." and replace with --Ferrajoli et al., "WP1066 disrupts janus kinase-2 and induces caspase-dependent apoptosis in acute myelogenous leukemia cells," *Cancer Research*, 67(23): 11291-11299, 2007.-- therefor.

In title page, item (56) References Cited - Other Publications, delete the 39th reference on page 2 "Garciaet al., "Constitutive activation of Stat3 by the Src and JAK tyrosine kinases participates in growth regulation of human breast carcinoma cells," *Oncogene*, 20:2499-2513, 2001." and replace with --Garcia et al., "Constitutive activation of Stat3 by the Src and JAK tyrosine kinases participates in growth regulation of human breast carcinoma cells," *Oncogene*, 20:2499-2513, 2001.-- therefor.

In title page, item (56) References Cited - Other Publications, delete the 40th reference on page 2 "Gazitet al., "Tyrphostins. 2. Heterocyclic and alpha-substituted benzylidenomalononitrile tyrphostins as potent inhibitors of EG receptor and ErbB2/nue tyrosine kinases," *J Med. Chem.*, 34(6):1896-1907, 1991." and replace with --Gazit et al., "Tyrphostins. 2. Heterocyclic and alpha-substituted benzylidenomalononitrile tyrphostins as potent inhibitors of EG receptor and ErbB2/nue tyrosine kinases," *J Med. Chem.*, 34(6):1896-1907, 1991.-- therefor.

CERTIFICATE OF CORRECTION (continued)
U.S. Pat. No. 8,637,675 B2

In title page, item (56) References Cited - Other Publications, delete the 41st reference on page 2 "Gazit,et al., "Tyrphostins I: synthesis and biological activity of protein tyrosine kinase inhibitors," *J Med. Chem.*, 32:2344-2352, 1989." and replace with --Gazit et al., "Tyrphostins I: synthesis and biological activity of protein tyrosine kinase inhibitors," *J Med. Chem.*, 32:2344-2352, 1989.--therefor.

In title page, item (56) References Cited - Other Publications, delete the 42nd reference on page 2 "Halleket al., "Multiple myeloma: increasing evidence for a multistep transformation process," *Blood*, 91(1):3-21, 1998." and replace with --Hallek et al., "Multiple myeloma: increasing evidence for a multistep transformation process," *Blood*, 91(1):3-21, 1998.-- therefor.

In title page, item (56) References Cited - Other Publications, delete the 44th reference on page 2 "Heinrichet al., "Interleukin-6-type cytokine signaling through the GP130/Jak/STAT pathway 1," *Biochem J.*, 334:297-314, 1998." and replace with --Heinrich et al., "Interleukin-6-type cytokine signaling through the GP130/Jak/STAT pathway 1," *Biochem J.*, 334:297-314, 1998.-- therefor.

In title page, item (56) References Cited - Other Publications, delete the 45th reference on page 2 "Hernandezet al., "2-cyano-N-furfuryl-3-(2-furyl)acrylamide," *Acta Crystallographica, Section C: Crystal Structure Communications*, C52(1):203-205, 1996." and replace with --Hernandez et al., "2-cyano-N-furfuryl-3-(2-furyl)acrylamide," *Acta Crystallographica, Section C: Crystal Structure Communications*, C52(1):203-205, 1996.-- therefor.

In title page, item (56) References Cited - Other Publications, delete the 46th reference on page 2 "Hideshimaet al., "NF-kappa B as a therapeutic target in multiple myeloma," *J. Biol. Chem.*, 277(19): 16639-16647, 2002." and replace with --Hideshima et al., "NF-kappa B as a therapeutic target in multiple myeloma," *J. Biol. Chem.*, 277(19): 16639-16647, 2002.-- therefor.

In title page, item (56) References Cited - Other Publications, delete the 47th reference on page 2 "Horiguchiet al., "STAT3 inhibitor WP1066 as a novel therapeutic agent for renal cell carcinoma," *British Journal of Cancer*, 102(11):1592-1599, 2010." and replace with --Horiguchi et al., "STAT3 inhibitor WP1066 as a novel therapeutic agent for renal cell carcinoma," *British Journal of Cancer*, 102(11):1592-1599, 2010.-- therefor.

In title page, item (56) References Cited - Other Publications, delete the 49th reference on page 2 "Hussainet al., "A novel small molecule inhibitor of signal transducers and activators of transcription 3 reverses immune tolerance in malignant glioma patients," *Cancer Research*, 67(20):9630-9636, 2007." and replace with --Hussain et al., "A novel small molecule inhibitor of signal transducers and activators of transcription 3 reverses immune tolerance in malignant glioma patients," *Cancer Research*, 67(20):9630-9636, 2007.-- therefor.

In title page, item (56) References Cited - Other Publications, delete the 1st reference on page 3 "Iwamaruet al., "A novel inhibitor of the STAT3 pathway induces apoptosis in malignant glioma cells both in vitro and in vivo," *Oncogene*, 26(17):2435-2444, 2007." and replace with --Iwamaru et al., "A novel inhibitor of the STAT3 pathway induces apoptosis in malignant glioma cells both in vitro and in vivo," *Oncogene*, 26(17):2435-2444, 2007.-- therefor.

In title page, item (56) References Cited - Other Publications, delete the 2nd reference on page 3

CERTIFICATE OF CORRECTION (continued)
U.S. Pat. No. 8,637,675 B2

"Jernberg-Wiklundet al., "Expression of myc-family genes in established human multiple myeloma cell lines: L-myc but not c-myc gene expression in the U-266 myeloma cell line," *Int. J. Cancer*, 51(1):116-123, 1992." and replace with --Jernberg-Wiklund et al., "Expression of myc-family genes in established human multiple myeloma cell lines: L-myc but not c-myc gene expression in the U-266 myeloma cell line," *Int. J. Cancer*, 51(1):116-123, 1992.-- therefor.

In title page, item (56) References Cited - Other Publications, delete the 4th reference on page 3 "Kerret al., "Of JAKs, STATs, blind watchmakers, jeeps and trains," *FEBS Lett.*, 546(1):1-5, 2003." and replace with --Kerr et al., "Of JAKs, STATs, blind watchmakers, jeeps and trains," *FEBS Lett.*, 546(1):1-5, 2003.-- therefor.

In title page, item (56) References Cited - Other Publications, delete the 5th reference on page 3 "Kijimaet al., "STAT3 activation abrogates growth factor dependence and contributes to head and neck squamous cell carcinoma tumor growth in vivo," *Cell Growth Differ*, 13:355-362, 2002." and replace with --Kijima et al., "STAT3 activation abrogates growth factor dependence and contributes to head and neck squamous cell carcinoma tumor growth in vivo," *Cell Growth Differ*, 13:355-362, 2002.-- therefor.

In title page, item (56) References Cited - Other Publications, delete the 6th reference on page 3 "Kirkenet al., "Tyrphostin AG0490 inhibits cytokine-mediated JAK3/STATSa/b signal transduction and cellular proliferation of antigen activated human T cells," *J.Leukoc. Biol.*, 65:891-899, 1999." and replace with --Kirken et al., "Tyrphostin AG0490 inhibits cytokine-mediated JAK3/STATSa/b signal transduction and cellular proliferation of antigen activated human T cells," *J. Leukoc. Bio.*, 65:891-899, 1999.-- therefor.

In title page, item (56) References Cited - Other Publications, delete the 7th reference on page 3 "Kisselevaet al., "Signaling through the JAK/STAT pathway, recent advances and future challenges," *Gene*, 285:1-24, 2002." and replace with --Kisseleva et al., "Signaling through the JAK/STAT pathway, recent advances and future challenges," *Gene*, 285:1-24, 2002.-- therefor.

In title page, item (56) References Cited - Other Publications, delete the 8th reference on page 3 "Konget al., "A novel inhibitor of signal transducers and activators of transcription 3 activation is efficacious against established central nervous system melanoma and inhibits regulatory T cells," *Clinical Cancer Research*, 14(18):5759-5768, 2008." and replace with --Kong et al., "A novel inhibitor of signal transducers and activators of transcription 3 activation is efficacious against established central nervous system melanoma and inhibits regulatory T cells," *Clinical Cancer Research*, 14(18):5759-5768, 2008.-- therefor.

In title page, item (56) References Cited - Other Publications, delete the 9th reference on page 3 "Konget al., "A novel phosphorylated STAT3 inhibitor enhances T cell cytotoxicity against melanoma through inhibition of regulatory T cells," *Cancer Immunology Immunotherapy*, 58(7): 1023-1032, 2009." and replace with --Kong et al., "A novel phosphorylated STAT3 inhibitor enhances T cell cytotoxicity against melanoma through inhibition of regulatory T cells," *Cancer Immunology Immunotherapy*, 58(7): 1023-1032, 2009.-- therefor.

In title page, item (56) References Cited - Other Publications, delete the 10th reference on page 3

"Kuehlet al., "Dysregulation of c-myc in multiple myeloma," *Curr. Top Microbiol. Immunol.*, 224:277-282, 1997." and replace with --Kuehl et al., "Dysregulation of c-myc in multiple myeloma," *Curr. Top Microbiol. Immunol.*, 224:277-282, 1997.-- therefor.

In title page, item (56) References Cited - Other Publications, delete the 11th reference on page 3 "Kupfermanet al., "Therapeutic suppression of constitutive and inducible JAK/STAT activation in head and neck squamous cell carcinoma," *Journal of Experimental Therapeutics and Oncology*, 8(2):117-127, 2009." and replace with --Kupferman et al., "Therapeutic suppression of constitutive and inducible JAK/STAT activation in head and neck squamous cell carcinoma," *Journal of Experimental Therapeutics and Oncology*, 8(2):117-127, 2009.-- therefor.

In title page, item (56) References Cited - Other Publications, delete the 12th reference on page 3 "Leeet al., "Flavopiridol disrupts STAT3/DNA interactions, attenuates STAT3-directed transcription, and combines with the Jak kinase inhibitor AG490 to achieve cytotoxic synergy," *Mol Cancer Ther*, 5(1):138-148, 2006." and replace with --Lee et al., "Flavopiridol disrupts STAT3/DNA interactions, attenuates STAT3-directed transcription, and combines with the Jak kinase inhibitor AG490 to achieve cytotoxic synergy," *Mol Cancer Ther*, 5(1):138-148, 2006.-- therefor.

In title page, item (56) References Cited - Other Publications, delete the 14th reference on page 3 "Levyet al., "STAT3: a multifaceted oncogene," *PNAS*, 103(27): 10151-10152, 2006." and replace with --Levy et al., "STAT3: a multifaceted oncogene," *PNAS*, 103(27): 10151-10152, 2006.-- therefor.

In title page, item (56) References Cited - Other Publications, delete the 15th reference on page 3 "Levyet al., "What does stat3 do?," *The Journal of Clinical Investigation*, 109(9), 2002." and replace with --Levy et al., "What does stat3 do?" *The Journal of Clinical Investigation*, 109(9):1143-1148, 2002.-- therefor.

In title page, item (56) References Cited - Other Publications, delete the 16th reference on page 3 "Lieberet al., "Establishment of a continuous tumor-cell line (panc-1) from a human carcinoma of the exocrine pancreas," *Int. J Cancer*, 15(5):741-747, 1975." and replace with --Lieber et al., "Establishment of a continuous tumor-cell line (panc-1) from a human carcinoma of the exocrine pancreas," *Int. J. Cancer*, 15(5):741-747, 1975.-- therefor.

In title page, item (56) References Cited - Other Publications, delete the 18th reference on page 3 "Liuet al., "Immunohistochemical localization of activated stat3 and hTERT protein in psoriasis vulgaris," *Eur J Dermatol.*, 16(2):205-206, 2006." and replace with --Liu et al., "Immunohistochemical localization of activated stat3 and hTERT protein in psoriasis vulgaris," *Eur. J. Dermatol.*, 16(2):205-206, 2006.-- therefor.

In title page, item (56) References Cited - Other Publications, delete the 20th reference on page 3 "Morganet al., "Human cell line (colo 357) of metastatic pancreatic adenocarcinoma," *Int. J Cancer*, 25(5):591-598, 1980." and replace with --Morgan et al., "Human cell line (colo 357) of metastatic pancreatic adenocarcinoma," *Int. J. Cancer*, 25(5):591-598, 1980.-- therefor.

In title page, item (56) References Cited - Other Publications, delete the 21st reference on page 3 "Murataet al., "Synthesis and structure-activity relationships of novel IKK-b inhibitors, Part 3: orally active anti-inflammatory agents," *Bioorganic & Medicinal Chemistry Letters*, 14:4019-4022, 2004." and replace with --Murata et al., "Synthesis and structure-activity relationships of novel IKK-b inhibitors, Part 3: orally active anti-inflammatory agents," *Bioorganic & Medicinal Chemistry Letters*, 14:4019-4022, 2004.-- therefor.

In title page, item (56) References Cited - Other Publications, delete the 22nd reference on page 3 "Nielsenet al., "Constitutive activation of a slowly migrating isoform of Stat3 in mycosis fungoides: Tyrphostin AG490 inhibits Stat3 activation and growth of mycosis fungoides tumor cell lines," *Proc. Natl. Acad. Sci. USA*, 94:6764-6769, 1997." and replace with --Nielsen et al., "Constitutive activation of a slowly migrating isoform of Stat3 in mycosis fungoides: Tyrphostin AG490 inhibits Stat3 activation and growth of mycosis fungoides tumor cell lines," *Proc. Natl. Acad. Sci. USA*, 94:6764-6769, 1997.-- therefor.

In title page, item (56) References Cited - Other Publications, delete the 23rd reference on page 3 "Nikitakiset al., "Targeting the STAT pathway in head and neck cancer: recent advances and future prospects," *Current Cancer Drug Targets*, 4:637-651, 2004." and replace with --Nikitakis et al., "Targeting the STAT pathway in head and neck cancer: recent advances and future prospects," *Current Cancer Drug Targets*, 4:637-651, 2004.-- therefor.

In title page, item (56) References Cited - Other Publications, delete the 24th reference on page 3 "Niuet al., "Roles of activated Src and Stat3 signaling in melanoma tumor cell growth," *Oncogene*, 21(46):7001-7010, 2002." and replace with --Niu et al., "Roles of activated Src and Stat3 signaling in melanoma tumor cell growth," *Oncogene*, 21(46):7001-7010, 2002.-- therefor.

In title page, item (56) References Cited - Other Publications, delete the 56th reference on page 3 "Pomeset al., "Structure of N-(2-furfuryl)-2-cyano-3-(5-nitro-2-furyl)acrylamide," *Anales de la Asociacion Quimica Argentina*, 82(4):249-255, 1994." and replace with --Pomes et al., "Structure of N-(2-furfuryl)-2-cyano-3-(5-nitro-2-furyl)acrylamide," *Anales de la Asociacion Quimica Argentina*, 82(4):249-255, 1994.-- therefor.

In title page, item (56) References Cited - Other Publications, delete the 1st reference on page 4 "Rahamanet al., "Inhibition of constitutively active Stat3 suppresses proliferation and induces apoptosis in glioblastoma multiforme cells," *Oncogene*, 21:8404-8413, 2002." and replace with --Rahaman et al., "Inhibition of constitutively active Stat3 suppresses proliferation and induces apoptosis in glioblastoma multiforme cells," *Oncogene*, 21:8404-8413, 2002.-- therefor.

In title page, item (56) References Cited - Other Publications, delete the 2nd reference on page 4 "Renglinet al., "Miotic aberrations induced by carbaryl reflect tyrosine kinase inhibition with coincident up-regulation of serine/threonine protein phosphatase activity: implications for coordination of karyokinesis and cytokinesis," *Mutagenesis*, 14(3):327-334, 1999." and replace with --Renglin et al., "Miotic aberrations induced by carbaryl reflect tyrosine kinase inhibition with coincident up-regulation of serine/threonine protein phosphatase activity: implications for coordination of karyokinesis and cytokinesis," *Mutagenesis*, 14(3):327-334, 1999.-- therefor.
In title page, item (56) References Cited - Other Publications, delete the 3rd reference on page 4 "Saikachiet al., "Synthesis of furan derivatives. XVIII. 2-cyano-3(5-nitro-2-furyl)acrylamides and

CERTIFICATE OF CORRECTION (continued)
U.S. Pat. No. 8,637,675 B2 esters," *Chem. & Pharm. Bull.* (Tokyo), 7:453-456, 1959." and replace with --Saikachi et al., "Synthesis of furan derivatives. XVIII. 2-cyano-3(5-nitro-2-furyl)acrylamides and esters," *Chem. & Pharm. Bull.* (Tokyo), 7:453-456, 1959.-- therefor.

In title page, item (56) References Cited - Other Publications, delete the 4th reference on page 4 "Satyamoorthyet al., "Melanoma cell lines from different stages of progression and their biological and molecular analyses," *Melanoma Res.*, 7(Suppl.2):S35-S42, 1997." and replace with --Satyamoorthy et al., "Melanoma cell lines from different stages of progression and their biological and molecular analyses," *Melanoma Res.*, 7(Suppl.2):S35-S42, 1997.-- therefor.

In title page, item (56) References Cited - Other Publications, delete the 5th reference on page 4 "Schepetkinet al., "Novel small-molecule inhibitors of anthrax lethal factor indentified by high-throughput screening," *Journal of Medicinal Chemistry*, 49(17):5232-5244, 2006." and replace with --Schepetkin et al., "Novel small-molecule inhibitors of anthrax lethal factor identified by high-throughput screening," *Journal of Medicinal Chemistry*, 49(17):5232-5244, 2006.-- therefor.

In title page, item (56) References Cited - Other Publications, delete the 6th reference on page 4 "Seidelet al., "Pharmaceutical intervention in the JAK/STAT signaling pathway," *Oncogene*, 19:2645-2656, 2000." and replace with --Seidel et al., "Pharmaceutical intervention in the JAK/STAT signaling pathway," *Oncogene*, 19:2645-2656, 2000.-- therefor.

In title page, item (56) References Cited - Other Publications, delete the 7th reference on page 4 "Selvanayagamet al., "Alternation and Abnormal Expression of the c-myc Oncogene in Human Multiple Myeloma," *Blood*, 71(1):30-35, 1988." and replace with --Selvanayagam et al., "Alternation and Abnormal Expression of the c-myc Oncogene in Human Multiple Myeloma," *Blood*, 71(1):30-35, 1988.-- therefor.

In title page, item (56) References Cited - Other Publications, delete the 9th reference on page 4 "Songet al., "Activation of Stat3 by receptor tyrosine kinases and cytokines regulates survival in human non-small cell carcinoma cells," *Oncogene*, 22:4150-4165, 2003." and replace with --Song et al., "Activation of Stat3 by receptor tyrosine kinases and cytokines regulates survival in human non-small cell carcinoma cells," *Oncogene*, 22:4150-4165, 2003.-- therefor.

In title page, item (56) References Cited - Other Publications, delete the 10th reference on page 4 "Songet al., "STAT signaling in head and neck cancer," *Oncogene*, 19:2489-2495, 2000." and replace with --Song et al., "STAT signaling in head and neck cancer," *Oncogene*, 19:2489-2495, 2000.-- therefor.

In title page, item (56) References Cited - Other Publications, delete the 11th reference on page 4 "Sunet al., "Cucurbitacin Q: a selective STAT3 activation inhibitors with potent antitumor activity," *Oncogene*, 24:3236-3245, 2005." and replace with --Sun et al., "Cucurbitacin Q: a selective STAT3 activation inhibitors with potent antitumor activity," *Oncogene*, 24:3236-3245, 2005.-- therefor.

In title page, item (56) References Cited - Other Publications, delete the 13th reference on page 4 "Tamizet al., "Structure-activity relationship of n-(phenylalkyl) cinnamides as novel NR2B

CERTIFICATE OF CORRECTION (continued)
U.S. Pat. No. 8,637,675 B2 subtype-selective NMDA receptor antagonists," *J. of Medicinal Chemistry*, 42:3412-20, 1999." and replace with --Tamiz et al., "Structure-activity relationship of n-(phenylalkyl) cinnamides as novel NR2B subtype-selective NMDA receptor antagonists," *J. of Medicinal Chemistry*, 42:3412-20, 1999.-- therefor.

In title page, item (56) References Cited - Other Publications, delete the 14th reference on page 4 "Tefferi et al., "JAK2 in myeloproliferative disorders is not just another kinase," *Cell Cycle*, 4(8):1053-1056, 2005." and replace with --Tefferi et al., "JAK2 in myeloproliferative disorders is not just another kinase," *Cell Cycle*, 4(8):1053-1056, 2005.-- therefor.

In title page, item (56) References Cited - Other Publications, delete the 16th reference on page 4 "Vermaet al., "Jak family of kinases in cancer," *Cancer Metastasis Rev.*, 22(4):423-434, 2003." and replace with --Verma et al., "Jak family of kinases in cancer," *Cancer Metastasis Rev.*, 22(4):423-434, 2003.-- therefor.

In title page, item (56) References Cited - Other Publications, delete the 17th reference on page 4 "Verstovseket al., "WP1066, a novel JAK2 inhibitor, suppresses proliferation and induces apoptosis in erythroid human cells carrying the JAK2 V617F mutation," *Clinical Cancer Research*, 14(3):788-796, 2008." and replace with --Verstovsek et al., "WP1066, a novel JAK2 inhibitor, suppresses proliferation and induces apoptosis in erythroid human cells carrying the JAK2 V617F mutation," *Clinical Cancer Research*, 14(3):788-796, 2008.-- therefor.

In title page, item (56) References Cited - Other Publications, delete the 18th reference on page 4 "Vezeridiset al., "Heterogeneity of potential for hematogenous metastasis in a human pancreatic carcinoma," *J. Surg. Res.*, 48(1):51-55, 1990." and replace with --Vezeridis et al., "Heterogeneity of potential for hematogenous metastasis in a human pancreatic carcinoma," *J. Surg. Res.*, 48(1):51-55, 1990.-- therefor.

In title page, item (56) References Cited - Other Publications, delete the 19th reference on page 4 "Vezeridiset al., "In vivo selection of a highly metastatic cell line from a human pancreatic carcinoma in the nude mouse," *Cancer*, 69(8):2060-2063, 1992." and replace with --Vezeridis et al., "In vivo selection of a highly metastatic cell line from a human pancreatic carcinoma in the nude mouse," *Cancer*, 69(8):2060-2063, 1992.-- therefor.

In title page, item (56) References Cited - Other Publications, delete the 21st reference on page 4 "Wanget al., "JAK3, STAT, and MAPK signaling pathways as novel molecular target for the tyrphostin AG-490 regulation of IL-2-mediated T cell response," *J. Immunol*, 162:3897-3904, 1999." and replace with --Wang et al., "JAK3, STAT, and MAPK signaling pathways as novel molecular target for the tyrphostin AG-490 regulation of IL-2-mediated T cell response," *J. Immunol.*, 162:3897-3904, 1999.-- therefor.

In title page, item (56) References Cited - Other Publications, delete the 22nd reference on page 4 "Xieet al., "Activation of Stat3 in human melanoma promotes brain metastasis," *Cancer Res.*,

CERTIFICATE OF CORRECTION (continued)
U.S. Pat. No. 8,637,675 B2

66(6)3186-3196, 66(6)3186-3196, 2006." and replace with --Xie et al., "Activation of Stat3 in human melanoma promotes brain metastasis," *Cancer Res.*, 66(6):3186-3196, 2006.-- therefor.

In title page, item (56) References Cited - Other Publications, delete the 23rd reference on page 4 "Xieet al., "Stat3 activation regulates the expression of matrix metalloproteinase-2 and tumor invasion and metastasis," *Oncogene*, 23:3550-3560, 2004." and replace with --Xie et al., "Stat3 activation regulates the expression of matrix metalloproteinase-2 and tumor invasion and metastasis," *Oncogene*, 23:3550-3560, 2004.-- therefor.

In title page, item (56) References Cited - Other Publications, delete the 25th reference on page 4 "Zlotniket al., "Tyrphostins reduce chemotherapy-induced intestinal injury in mice: assessment by a biochemical assay," *Br. J. Cancer*, 92(2):294-297, 2005." and replace with --Zlotnik et al., "Tyrphostins reduce chemotherapy-induced intestinal injury in mice: assessment by a biochemical assay," *Br. J. Cancer*, 92(2):294-297, 2005.-- therefor.

In title page, item (56) References Cited - Other Publications, delete the 6th reference on page 5 "Chakraborty et al., "A novel Jak2/STAT3 pathway inhibitor promotes apoptosis and blocks growth of bladder cancer cells," *Proc 98$_{th}$ Amer Assoc Cancer Res Annual Meeting*, Los Angeles, CA, 2007." and replace with --Chakraborty et al., "A novel Jak2/STAT3 pathway inhibitor promotes apoptosis and blocks growth of bladder cancer cells," *Proc 98$^{th}$ Amer Assoc Cancer Res Annual Meeting*, Los Angeles, CA, 2007.-- therefor.

In title page, item (56) References Cited - Other Publications, delete the 28th reference on page 5 "Fujita et al , "Inhibition of STAT3 promotes the efficacy of adoptive transfer therapy using type-1 Ctis by modulation of the immunological microenvironment in a murine intracranial glioma," *J Immunol*, 180:2089-2098, 2008." and replace with --Fujita et al., "Inhibition of STAT3 promotes the efficacy of adoptive transfer therapy using type-1 Ctis by modulation of the immunological microenvironment in a murine intracranial glioma," *J. Immunol.*, 180:2089-2098, 2008.-- therefor.

In title page, item (56) References Cited - Other Publications, delete the 32nd reference on page 5 "Gong et al., "Expression of activated signal transducer and activator of transcription 3 predicts expression of vascular endothelial growth factor in and angiogenic phenotype of human gastric cancer," *Clin Cancer Res*, 11:1386-1393, 2005." and replace with --Gong et al., "Expression of activated signal transducer an activator of transcription 3 predicts expression of vascular endothelial growth factor in and angiogenic phenotype of human gastric cancer," *Clin. Cancer Res.*, 11:1386-1393, 2005.-- therefor.

In title page, item (56) References Cited - Other Publications, delete the 40th reference on page 5 "Heimberger et al., "An epidermal growth factor receptor variant Iii peptide vaccination appears promising in newly diagnosed GBM patients: preliminary results of a randomized phase II clinical trial," *74$^{th}$ Annual Meeting of the American Association of Neurological Surgeons*, San Francisco, CA, 2006." and replace with --Heimberger et al., "An epidermal growth factor receptor variant III peptide vaccination appears promising in newly diagnosed GBM patients: preliminary results of a randomized phase II clinical trial," *74$^{th}$ Annual Meeting of the American Association of Neurological Surgeons*, San Francisco, CA, 2006.-- therefor.

CERTIFICATE OF CORRECTION (continued)
U.S. Pat. No. 8,637,675 B2

In title page, item (56) References Cited - Other Publications, delete the 19th reference on page 6 "Krebs et al., "SOCS proteins: negative regulators of cytokine signaling," *Stem Cells*, 19:378387, 2001." and replace with --Krebs et al., "SOCS proteins: negative regulators of cytokine signaling," *Stem Cells*, 19:378-387, 2001.-- therefor.

In title page, item (56) References Cited - Other Publications, delete the 24th reference on page 6 "Lassmann et al., "STAT3 mRNA and protein expression in colorectal cancer: effects on STAT3-inducible targets linked to cell survival and proliferation," *J Clin Pathol*, 60:173179, 2007." and replace with --Lassmann et al., "STAT3 mRNA and protein expression in colorectal cancer: effects on STAT3-inducible targets linked to cell survival and proliferation," *J. Clin. Pathol.*, 60:173-179, 2007.-- therefor.

In title page, item (56) References Cited - Other Publications, delete the 35th reference on page 6 "Madden et al., "The preclinical pharmacology of WP1066, a potent small molecule inhibitor of the JAK2/STAT3 pathway," *Proc $97_{th}$ Amer Assoc Cancer Res Annual Meeting*, Washington DC, 2006." and replace with --Madden et al., "The preclinical pharmacology of WP1066, a potent small molecule inhibitor of the JAK2/STAT3 pathway," *Proc $97^{th}$ Amer Assoc Cancer Res Annual Meeting*, Washington DC, 2006.-- therefor.

In title page, item (56) References Cited - Other Publications, delete the 18th reference on page 7 "PCT International Preliminary Report on Patentability issued in International Application." and replace with --PCT International Preliminary Report on Patentability issued in International Application No. PCT/US2010/059005, issued June 5, 2012.-- therefor.

In title page, item (56) References Cited - Other Publications, delete the 28th reference on page 7 "Rosenberg er al., "Cancer immunotherapy: moving beyond current vaccines," *Nat Med*, 10:909-915, 2004." and replace with --Rosenberg et al., "Cancer immunotherapy: moving beyond current vaccines," *Nat Med*, 10:909-915, 2004.-- therefor.

In title page, item (56) References Cited - Other Publications, delete the 41st reference on page 7 "Siddiquee et al., "An oxazole-based small-molecule Stat3 inhibitor modulates STAT3 stability and processing and induces antitumor cell effects," *ACS Chemical Biology*, 787798, 2007." and replace with --Siddiquee et al., "An oxazole-based small-molecule Stat3 inhibitor modulates STAT3 stability and processing and induces antitumor cell effects," *ACS Chemical Biology*, 2:787-798, 2007.-- therefor.

In title page, item (56) References Cited - Other Publications, delete the 42nd reference on page 7 "Siddiquee et al., "Selective chemical probe inhibitor of STAT3, identified through structure-based virtual screening, induces antitumor activity," *Proc Natl Acad Sci USA*, 104:73917396, 2007." and replace with --Siddiquee et al., "Selective chemical probe inhibitor of STAT3, identified through structure-based virtual screening, induces antitumor activity," *Proc Natl Acad Sci USA*, 104:7391-7396, 2007.-- therefor.

In title page, item (56) References Cited - Other Publications, delete the 11th reference on page 8 "Yang et al., "Altered p-STAT3 (Tyr705) expression is associated with histological grading and intratumour microvessel density in hepatocellular carcinoma," *J Clin Pathol*, 60:642648, 2007." and replace with --Yang et al., "Altered p-STAT3 (Tyr705) expression is associated with histological grading and intratumour microvessel density in hepatocellular carcinoma," *J Clin Pathol*, 60:642-648, 2007.-- therefor.

In the Claims

In claim 1, column 33, lines 44-50, delete the entire contents of lines 44-50 and replace with

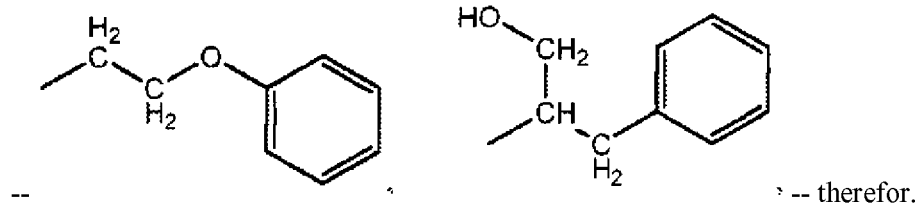

-- therefor.

In claim 1, column 33, line 53, delete "charide" and replace with --charide,-- therefor.

In claim 12, column 34, line 52, after composition, delete "comprising".

In claim 16, column 34, line 64, after composition, delete "comprising".